(12) United States Patent
Bergstein et al.

(10) Patent No.: US 12,357,678 B2
(45) Date of Patent: *Jul. 15, 2025

(54) CANCER STEM CELL TARGETED CANCER VACCINES

(71) Applicant: Stemline Therapeutics, Inc., New York, NY (US)

(72) Inventors: Ivan Bergstein, New York, NY (US); Christopher Brooks, Brooklyn, NY (US); Thomas P. Cirrito, Long Island City, NY (US)

(73) Assignee: Stemline Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,774

(22) Filed: Apr. 28, 2023

(65) Prior Publication Data

US 2024/0115677 A1    Apr. 11, 2024

Related U.S. Application Data

(63) Continuation of application No. 16/599,031, filed on Oct. 10, 2019, now Pat. No. 11,672,847, which is a continuation of application No. 14/401,053, filed as application No. PCT/US2013/041063 on May 15, 2013, now Pat. No. 10,485,858.

(60) Provisional application No. 61/647,615, filed on May 16, 2012.

(51) Int. Cl.
| | | |
|---|---|---|
| *A61K 38/20* | (2006.01) | |
| *A61K 31/437* | (2006.01) | |
| *A61K 38/16* | (2006.01) | |
| *A61K 38/17* | (2006.01) | |
| *A61K 38/19* | (2006.01) | |
| *A61K 38/21* | (2006.01) | |
| *A61K 38/30* | (2006.01) | |
| *A61K 38/45* | (2006.01) | |
| *A61K 39/00* | (2006.01) | |
| *C07K 14/33* | (2006.01) | |
| *C07K 14/47* | (2006.01) | |
| *C07K 14/54* | (2006.01) | |
| *C12N 9/12* | (2006.01) | |

(52) U.S. Cl.
CPC ........ *A61K 38/2086* (2013.01); *A61K 31/437* (2013.01); *A61K 38/164* (2013.01); *A61K 38/1761* (2013.01); *A61K 38/193* (2013.01); *A61K 38/2013* (2013.01); *A61K 38/21* (2013.01); *A61K 38/30* (2013.01); *A61K 38/45* (2013.01); *A61K 39/0011* (2013.01); *A61K 39/001119* (2018.08); *A61K 39/001122* (2018.08); *A61K 39/00115* (2018.08); *C07K 14/33* (2013.01); *C07K 14/4747* (2013.01); *C07K 14/5437* (2013.01); *C12N 9/12* (2013.01); *A61K 2039/55511* (2013.01); *A61K 2039/55522* (2013.01); *A61K 2039/572* (2013.01); *A61K 2039/80* (2018.08); *C12Y 207/10001* (2013.01)

(58) Field of Classification Search
CPC .... A61K 39/001119; A61K 39/001122; A61K 39/00115; A61K 38/193; A61K 38/2086
See application file for complete search history.

(56) References Cited

U.S. PATENT DOCUMENTS

| | | |
|---|---|---|
| 5,057,540 A | 10/1991 | Kensil et al. |
| 5,595,756 A | 1/1997 | Bally et al. |
| 6,162,432 A | 12/2000 | Wallner et al. |
| 7,297,337 B2 | 11/2007 | Storkus et al. |
| 7,338,929 B2 | 3/2008 | Debinski et al. |
| 7,354,584 B2 | 4/2008 | Reed et al. |
| 7,612,162 B2 | 11/2009 | Okada et al. |
| 7,842,294 B2 | 11/2010 | Andersen et al. |
| 7,902,143 B2 | 3/2011 | Okano |
| 7,943,138 B2 | 5/2011 | Ciesielski et al. |
| 8,097,256 B2 | 1/2012 | Yu et al. |
| 8,114,407 B2 | 2/2012 | Storkus et al. |
| 8,859,488 B2 | 10/2014 | Okada et al. |
| 10,434,155 B2 | 10/2019 | Okada et al. |
| 10,485,585 B2 | 11/2019 | Solomon et al. |
| 10,485,858 B2 | 11/2019 | Bergstein et al. |
| 2002/0168360 A1 | 11/2002 | Dingivan et al. |
| 2002/0182219 A1 | 12/2002 | Debinski et al. |
| 2005/0002934 A1 | 1/2005 | Reed |

(Continued)

FOREIGN PATENT DOCUMENTS

| | | |
|---|---|---|
| EP | 2849772 A4 | 3/2015 |
| EP | 3536334 A1 | 9/2019 |

(Continued)

OTHER PUBLICATIONS

Bowie et al. Deciphering the Message in Protein Sequences: Tolerance to Amino Acid Substitutions. Science, 1990, 247:1306-1310 (Year: 1990).*

(Continued)

*Primary Examiner* — Sandra Carter
(74) *Attorney, Agent, or Firm* — McNeill PLLC

(57) ABSTRACT

Provided herein are cancer stem cell targeted cancer vaccines and methods for treating and vaccinating against cancer. Also contained herein are regimens by which cancer stem cell targeted cancer vaccines are administered, such regimens comprising peptides, compositions, immunomodulatory agents, and emulsifiers. Also provided are the patient populations to which the regimens are to be administered, and the dosages, schedules, and route of administration for the regimens.

14 Claims, 8 Drawing Sheets

Specification includes a Sequence Listing.

(56) References Cited

U.S. PATENT DOCUMENTS

| | | | |
|---|---|---|---|
| 2005/0048550 | A1 | 3/2005 | Storkus et al. |
| 2005/0153923 | A1 | 7/2005 | Kinch |
| 2005/0281783 | A1 | 12/2005 | Kinch et al. |
| 2006/0034856 | A1 | 2/2006 | Kosmatopoulos et al. |
| 2006/0099652 | A1 | 5/2006 | Gately et al. |
| 2007/0167375 | A1 | 7/2007 | Okada et al. |
| 2008/0118432 | A1 | 5/2008 | Bergstein et al. |
| 2008/0118518 | A1 | 5/2008 | Cirrito et al. |
| 2008/0175870 | A1 | 7/2008 | Mather et al. |
| 2008/0311141 | A1 | 12/2008 | Yu et al. |
| 2009/0041732 | A1 | 2/2009 | Ciesielski et al. |
| 2009/0123371 | A1 | 5/2009 | Debinski et al. |
| 2010/0008940 | A1 | 1/2010 | Okada et al. |
| 2011/0091489 | A1 | 4/2011 | Andersen |
| 2011/0223187 | A1 | 9/2011 | Shahabi et al. |
| 2011/0229504 | A1 | 9/2011 | Fritsche et al. |
| 2012/0052080 | A1* | 3/2012 | Okada .................. A61K 38/17 514/19.3 |
| 2013/0295046 | A1 | 11/2013 | Okada |
| 2015/0258185 | A1 | 9/2015 | Okada |
| 2016/0114017 | A1 | 4/2016 | Okada |

FOREIGN PATENT DOCUMENTS

| | | | |
|---|---|---|---|
| JP | 2004353820 | A | 12/2004 |
| WO | 1993006866 | A2 | 4/1993 |
| WO | 1995022317 | A1 | 8/1995 |
| WO | 1996018409 | A1 | 6/1996 |
| WO | 1997049421 | A1 | 12/1997 |
| WO | 2001058479 | A1 | 8/2001 |
| WO | 2001062979 | A2 | 8/2001 |
| WO | 2002098370 | A2 | 12/2002 |
| WO | 2003091383 | A2 | 11/2003 |
| WO | 2006034334 | A2 | 3/2006 |
| WO | 2006062094 | A1 | 6/2006 |
| WO | 2007039192 | A2 | 4/2007 |
| WO | 2007053648 | A2 | 5/2007 |
| WO | 2007109812 | A2 | 9/2007 |
| WO | 2007109813 | A1 | 9/2007 |
| WO | 2008091908 | A2 | 7/2008 |
| WO | 2010037513 | A1 | 4/2010 |
| WO | 2012027379 | A2 | 3/2012 |
| WO | 2013173411 | A1 | 11/2013 |

OTHER PUBLICATIONS

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Lazar et al. Transforming Growth Factoralpha: Mutation of Aspartic Acid 47 and Leucine 48 Results in Different Biological Activities. Mol. Cell. Biol., 8:1247-1252, 1988 (Year: 1988).*

Whisstock et al. Prediction of proteinfunction fromprotein sequence and structure. Quarterly Reviews in Biophysics. 36(3):307-340, 2007 (Year: 2007).*

Liu et al., 2000, "Interleukin-13 sensitivity and receptor phenotypes of human glial cell lines: non-neoplastic glia and low-grade astrocytoma differ from malignant glioma," Cancer Immunol Immunother 49: 319-324.

Liu et al., 1994, Chemical ligation approach to form a peptide bond between unprotected peptide segments. concept and model study, Journal of the American Chemical Society, 116(10): 4149-4153.

Liu et al., 1994, "Peptide segment ligation strategy without use of protecting groups," Proc. Nat. Acad. Sci. USA, 91: 6584-6588.

Liu et al., 1996, "Acyl disulfide-mediated intramolecular acylation for orthogonal coupling between unprotected peptide segments, mechanism and application," Tetrahedron Letters, 37(7): 933-936.

Liu et al., 2004, "HER-2, gpl 00, and MAGE-1 are expressed in human glioblastoma and recognized by cytotoxic T Cells," Cancer Research, 64: 4980-4986.

Liu et al., 2006, "A genome-wide screen reveals functional gene clusters in the cancer genome and identified Epha2 as a mitogen in glioblastoma," Cancer Research, 66: 10815-10823.

Liu et al., 2006, "Analysis of gene expression and chemoresistance ofCD133+ cancer stem cells in glioblastoma", Molecular Cancer, 5(67):1-12.

Livak et al., 2001, "Analysis of relative gene expression data using real-time quantitative PCR and the 2-Mcr method," Methods, 25:402-408.

Logan et al., 1984, "Adenovirus tripartite leader sequence enhances translation of mRNAs late after infection," Proc. Nat. Acad. Sci. USA, 81: 3655-3659.

Lollini et al., 2006 "Vaccines for tumor prevention," Nature Review Cancer, 6(3): 204-16.

Long et al., 2009 "Magnetovaccination as a Novel Method to Assess and Quantify Dendritic Cell Tumor Antigen Capture and Delivery to Lymph Nodes," Cancer Research 69(7):3180-3187.

Lu et al., 1998, "Expression of a novel antiapoptosis gene, survivin, correlated with tumor cell apoptosis and p53 accumulation in gastric carcinomas", Cancer Research, 58: 1808-1812.

Lupetti et al., 1998, "Translation of a retained intron in tyrosinase-related protein (TRP) 2 mRNA generates a new cytotoxic t lymphocyte (CTL)-defined and shared human melanoma antigen not expressed in normal cells of the melanocytic lineage", The Journal of Experimental Medicine, 188(6): 1005-1016.

Mailliard et al., 2004, "a-type-1 polarized dendritic cells: a novel immunization tool with optimized CTL-inducing activity," Cancer Research, 64(17): 5934-5937.

Marincola et al., 2003, "Tumors as elusive targets of T-cell-based active immunotherapy", Trends in Immunology, 334-341.

Monsurro et al., 2002, "Functional heterogeneity of vaccine-induced CD8+ T cells," The Journal ofImmunology, 168: 5933-5942.

Mori et al., 2002, "Expression of the antiapoptosis gene survivin in human leukemia", Intl J Hematol, 75(2):161-165.

Morrison et al., 2008, "Breast cancer stem cells: implications for therapy of breast cancer", Breast Cancer Research, 10(4): 1-14.

Muthusw Amy et al., 2008, "Ability of mature dendritic cells to interact with regulatory T cells is imprinted during maturation," Cancer Research, 68(14): 5972-5978.

Nagaraj et al., (2007), "Dendritic Cell-based Full-length Survivin Vaccine in Treatment of Experimental Tumors," J Immunother 30(2): 169-179.

Nakagawa et al., 1985, "The use of polymer-bound oximes for the synthesis of large peptides usable in segment condensation: synthesis of a 44 amino acid amphiphilic peptide model of apolipoprotein A-1", J. Am. Chem. Soc., 107(24):7087-7092.

Nakahata et al, 2011, "Human Glioblastoma Cells Display Mesenchymal Stem Cell Features and Form Intracranial Tumors in Immunocompetent Rats," Journal of Stem Cells, 5(3): 1-9.

Naruse-Nakajima et al., 2001, "Involvement of EphA2 in the formation of the tail notochord via interaction with ephrinA 1," Mechanisms of Development, 102: 95-105.

Nasr et al., 2008, "Comparison of pHH3, Ki-67, and survivin immunoreactivity in benign and malignant melanocytic lesions", American Journal of Dermatopathology, 3(2):117-122.

Neeson and Paterson, 2006, "Effects of the tumor microenvironment on the efficacy of tumor immunotherapy", Immunological Investigations, 35:359-394.

Nishimura et al., 2006, "Adoptive transfer of type 1 CTL mediates effective anti-central nervous system tumor response: critical roles of IFN-inducible protein-10", Cancer Research, 66(8): 4478-4487.

Nishizawa et al., 2012, "HSP DNAJB8 controls tumor-initiating ability in renal cancer stem-like cells", Cancer Res, 72(11): 2844-2854.

Nutt et al., 2005, "YKL-40 is a differential diagnostic marker for histologic subtypes of high-grade gliomas," Clinical Cancer Research, 11: 2258-2264.

O'Connell et al., 2009, "Elucidating the elite: mechanisms of control in HIV-1 infection," Trends in Pharmacological Sciences, 30(12): 631-637.

(56) References Cited

OTHER PUBLICATIONS

Ogawa et al., 2000, "The ephrin-A1 ligand and its receptor, EphA2, are expressed during tumor neovascularization", Oncogene, 19(52):6043-6052.

Ogden et al., 2006, "Defective receptor expression and dendritic cell differentiation of monocytes in glioblastomas," Neurosurgery, 59(4): 902-910.

Okada et al., 2008, "Expression of glioma-associated antigens in pediatric brain stem and non-brain stem gliomas," Journal of Neurooncology 88(3): 245-50.

Okada et al., 1998, "Bone marrow-derived dendritic cells pulsed with a tumor-specific peptide elicit effective anti-tumor immunity against intracranial neoplasms", International Journal of Cancer, 78(1): 196-201.

Okada et al., 2001, "Cytokine gene therapy of gliomas: effective induction of therapeutic immunity to intracranial tumors by peripheral immunization with interleukin-4 transduced glioma cells", Gene Therapy, 8(15):1157-1166.

Okada et al., 2001, "Gene therapy of malignant gliomas: a pilot study of vaccination with irradiated autologous glioma and dendritic cells admixed with IL-4 transduced fibroblasts to elicit an immune response", Human Gene Therapy, 12(5):575-595.

Okada et al., 2003, "Autologous glioma cell vaccine admixed with interleukin-4 gene transfected fibroblasts in the treatment of recurrent glioblastoma: Preliminary observations in a patient with a favorable response to therapy", Journal of Neuro-Oncology, 64(1-2): 13-20.

Okada et al., 2007, "Autologous glioma cell vaccine admixed with interleukin-4 gene transfected fibroblasts in the treatment of patients with malignant gliomas," Journal of Translational Medicine, 5(67): 1-10.

Okada et al., 2009, "Immunotherapeutic Approaches for Glioma," Grit. Rev. Immunol., 29(1): 1-42.

Okada et al., 2011, "Induction of CD8 T-Cell Responses Against Novel Glioma-Associated Antigen Peptides and Clinical Activity by Vaccinations With a-Type 1 Polarized Dendritic Cells and Polyinosinic-Polycytidylic Acid Stabilized by Lysine and Carboxymethylcellulose in Patients With Recurrent Malignant Glioma," Journal of Clinical Oncology 29(3): 330-336 (data supplement).

Okada et al., 2014 "Induction of Robust Type-1 CD8 T-cell Responses in WHO Grade 2 Low-Grade Glioma Patients Receiving Peptide-Based Vaccines in Combination with Poly-ICLC," Clinical Cancer Research, pp. 286-294.

Okano et al., 2002, "Identification of a novel HLA _ A *0201-restricted, cytotoxic T lymphocyte epitope in a human glioma-associated antigen, interleukin 13 receptor a2 chain", Clinical Cancer Research, 8(9):2851-2855.

Pascolo et al., 1997, "HLA-A2.1-restricted education and cytolytic activity of CD8+ T lymphocytes from beta2 microglobulin (beta2m) HLA-A2.1 monochain transgenic H-2Db beta2m double knockout mice", The Journal of Experimental Medicine, 185(12):2043-2051.

Pelloski et al., 2005, "YKL-40 Expression is associated with poorer response to radiation and shorter overall survival in glioblastoma," Clinical Cancer Research, 11(9): 3326-3334.

Pennington et al., "Comparison of folding procedures on synthetic w-conotoxin," Peptides 1990, Proceedings of the Twenty-First European Peptide Symposium, (Giralt et al., eds) (Piatja d' Aro, Spain) (Sep. 2-8, 1990) (164-166).

Pollack et al., "Antigen-Specific Immune Responses and Clinical Outcome After Vaccination With Glioma-Associated Antigen Peptides and Polyinosinic-Polycytidylic Acid Stabilized by Lysine and Carboxymethylcellulose in Children with Newly Diagnosed Malignant Brainstem and Nonbrainstem Gliomas," Journal of Clinical Oncology 32(19): 2050-2059 (Jul. 1, 2014).

Pollack et al., 2002, "Expression of p53 and prognosis in children with malignant gliomas", The New England Journal of Medicine, 346(6): 420-427.

Pollack et al., 2016, "Immune responses and outcome after vaccination with glioma-associated antigen peptides and poly-ICLC in a pilot study for pediatric recurrent low-grade gliomas," Neuro-Oncology 18(9): 1157-1168.

Qiang et al., 2009, "Isolation and characterization of cancer stem like cells in human glioblastoma cell lines", Cancer Letters, 279(1): 13-21.

Rasala et al., 2010, "Production of therapeutic proteins in algae, analysis of expression of seven human proteins in the chloroplast of Chlamydomonas reinhardtii," Plant Biotechnology Journal, 8: 719-733.

Riker et al., 1999, "Immune selection after antigen-specific immunotherapy of melanoma", Surgery, 126(1): 112-120.

Eguchi et al., 2006, "Identification of interleukin-13 receptor a2 peptide analogues capable of inducing improved antiglioma CTL responses," Cancer Research, 66(11): 5883-5891.

Extended European Search Report dated Dec. 23, 2015 of European Application No. 13763504.1-1405.

Fallert et al., 2002, "Improved detection of simian immunodeficiency virus RNA by in situ hybridization in fixed issue sections: combined effects of temperatures for tissue fixation and probe hybridization," Journal of virological Methods, 99: 23-32.

Fichtner-Feigl et al., 2006, "IL-13 signaling through the IL-13a2 receptor is involved in induction of TGF-131 production and fibrosis," Nature Medicine, 12(1): 99-106.

Foecking et al., 2006, "Powerful and versatile enhancer-promoter unit for mammalian expression vectors," Gene 45: 101-105.

Francini et al., 2002, "High-affinity HLA-A(*)02.0I peptides from parathyroid hormone-related protein generate in vitro and in vivo antitumor CTL response without autoimmune side effects", The Journal of Immunology, 169(9):4840-4849.

Fujisawa et al., 2011, "Targeting IL-13Ra2 in human pancreatic ductal adenocarcinoma with combination therapy pfIL-13-PE and gemcitabine", International Journal of Cancer, 128(5): 1221-1231.

Fujita et al., 2009, "Effective immunotherapy against murine gliomas using type 1 polarizing dendritic cells-significant roles of CXCL 1 O," Cancer Research, 69(4): 1587-6683.

Garcia-Hernandez et al., 2008, "Prostate stem cell antigen vaccination induces a long-term protective immune response against prostate cancer in the absence of autoimmunity", Cancer Research, 68(3):861-869.

Gilliet et al., 2003, "Intranodal injection of semimature monocyte-derived dendritic cells induces T helper type 1 responses to protein neoantigen," Blood, 102(1): 36-42.

Grabowski et al., 2003, "Prognostic value of nuclear survivin expression in oesophageal squamous cell carcinoma", British J Can, 88:115-119.

Graff-Dubois et al., 2002, "Generation of CTL recognizing an HLA-A*0201-Restricted Epitope Shared by MAGE-A1, -A2, -A3, -A4, -A6, -A10, and -A12 tumor antigens: implication in a broad-spectrum tumor immunotherapy", The Journal of immunology, 169:575-580.

Greenspan et al., 1999, "Defining epitopes: it's not as easy as it seems", Nature Biotechnology, 17:936-937.

Greten et al., 2002, "Peptide-?2-microglobulin-MHC fusion molecules bind antigen-specific T cells and can be used for multivalent MHC-lg complexes", Journal of immunological Methods, 271:125-135.

Gross et al., 2004, "High vaccination efficiency of low-affinity epitopes in antitumor immunotherapy", The Journal of Clinical Investigation, 113(3):425-433.

Gura, 1997, "Systems for identifying new drugs are often faulty", Science, 278:1041-1042.

Hatano et al., 2004, "Vaccination with EphA2-derived T cell-epitopes promotes immunity against both EphA2-expressing and EphA2-negative tumors", Journal of Translational Medicine, 2(40):1-9.

Hatano et al., 2005, "EphA2 as a glioma-associated antigen: a novel target for glioma vaccines," Neoplasia, 7(8): 717-722.

Heppner et al., 1983, "Tumor heterogeneity: biological implications and therapeutic consequences," Cancer Metastasis Review 2:5-23.

(56) References Cited

OTHER PUBLICATIONS

Herrem et al., 2005, "Expression of EphA2 is prognostic of disease-free interval and overall survival in surgically treated patients with renal cell carcinoma", Clinical Cancer Research, 11(1 ):226-31.
Ikeguchi et al., 2002, "Expression of survivin messenger RNA correlates with poor prognosis in patients with hepatocellular carcinoma", Diagnostic Molecular Pathology, 11(1):33-40.
U.S. Appl. No. 13/215,938.
U.S. Appl. No. 13/925,093.
U.S. Appl. No. 14/478,458.
U.S. Appl. No. 14/515,939.
U.S. Appl. No. 14/688,376.
U.S. Appl. No. 14/951,821.
U.S. Appl. No. 16/572,019.
Inouye et al., 1985, "Up-promoter mutations in the lpp gene *Escherichia coli*," Nucleic Acids Research, 13(9): 3101-3110.
Ito et al., 2000, "Survivin promotes cell proliferation in human hepatocellular carcinoma", Hepatology, 31: 1080-1085.
Izumoto et al., 2008, "Phase II clinical trial of Wilms tumor 1 peptide vaccination for patients with recurrent glioblastoma multiforme," J. Neurosurg., 108: 963-971.
Jain, 1994, "Barriers to drug delivery in solid tumors," Scientific American, pp. 58-65.
Joshi et al., 2000, "Interleukin-13 Receptor a Chain: A Novel Tumor-associated Transmembrane Protein in Primary Explants of Human Malignant Gliomas," Cancer Research 60:1168-1172.
Kaiser, 2006, "First pass at cancer genome reveals complex landscape", Science, 313:1370.
Kalinski et al., 1987, "IL-12-deficient dendritic cells, generated in the presence of prostaglandin E2, promote type 2 cytokine production in maturing human naive T helper cells," The Journal of Immunology, 159(1): 28-35.
Kalinski et al., 1999, "Final maturation of dendritic cells is associated with impaired responsiveness to IFN-y and to bacterial IL-12 inducers: decreased ability of mature dendritic cells to produce IL-12 during the interaction with Th cells," The Journal of immunology, 162(6): 3231-3236.
Kalinski et al., 2010, "Polarized dendritic cells as cancer vaccines: directing effector-type T cells to tumors," Semin. Immunol., 22(3): 173-182.
Kamber et al., 1980, "The Synthesis of cystine peptides by iodine oxidation of s-trityl-cysteine and s-acetamidomethyl-cysteine peptides," Helvetica Chimica Acta, 63(4):899-915.
Kikuchi et al., 2004, "Vaccination of glioma Patients with Fusions of dendritic and Glioma Cells and Recombinant Human Interleukin 12," J. Immunother, 27(6): 452-459.
Kinch et al., 2003, "Overexpression and functional alterations of the EphA2 tyrosine kinase in cancer", Clinical & Experimental Metastasis, 20:59-68.
Kirkin et al., 1998, Melanoma-associated antigens recognized by cytotoxic T lymphocytes, APMIS, 106:665-679.
Kirkwood et al., 2009, "immunogenicity and antitumor effects of vaccination with peptide vaccine+/- granulocyte-monocyte colony-stimulating factor and/or IFNa2b in advanced metastatic melanoma: eastern cooperative oncology group phase II Trial El696," Clinical Cancer Research, 15(4): 1443-1451.
Koch et al., 1985, "An abundant ubiquitous glycoprotein (GP100) in nucleated mammalian cells," FEBS Letters, 179(2): 294-298.
Kondo et al., 2004, "Persistence of a small population of cancer stem-like cells in the C6 glioma cell line", Proc Natl Acad Sci USA, 101:781-786.
Kouklis et al., 1993, "In vitro assembly properties of vimentin mutagenized at the beta-site tail motif," J Cell Science, 106(pt 3):919-928.
Lazar et al., 1988 "Transforming Growth Factor ox: Mutation of Aspartic Acid 47 and Leucine 48 Results in Different Biological Activities," Mol. Cell. Biol 8:1247-1252.

Lehner et al., 2002, "Immunohistochemical localization of the IAP protein survivin in bladder mucosa and transitional cell carcinoma", Applied Immunohistochemistry & Molecular Morphology, 10(2): 134-138.
Li et al., 1999, "Loss of adenoviral receptor expression in human bladder cancer cells: a potential impact on the efficacy of gene therapy", Cancer Res, 59:325-330.
Li et al., 2007 "Expression of EphA2 in Human Astrocytic Tumors: Correlation with Pathologic Grade, Proliferation and Apoptosis," Tumor Biology 28, pp. 165-172 (2007).
Liau et al., 2005, "Dendritic cell vaccination in glioblastoma patients induces systemic and intracranial T-cell responses modulated by the local central nervous system tumor microenvironment," Clinical Cancer Research, 11(15): 5515-5525.
Rodrigues et al., 2010, "Normal human monocytes exposed to glioma cells acquire myeloid-derived suppressor cell-like properties," Neuro-Oncology, 12(4): 351-365.
Rong et al, 2011, "EphA2-Dependent Molecular Targeting Therapy for Malignant Tumors," Current Cancer Drug Targets, 11: 1082-1097.
Ruther et al., 1983, "Easy identification of eDNA clones," The EMBO Journal, 2(10): 1791-1794.
Saikali et al., 2007, "Expression of nine tumour antigens in a series of human glioblastoma multiforme: interest of EGFRvIII, IL-13Ra2, gplOO and TRP-2 for immunotherapy," J. Neurooncol. 81: 139-148.
Sainio et al., 1997, "Differential regulation of two sets of mesonephric tubules by WT-1", Development, 124: 1293-1299.
Salazar et al., 1996, "Long-term treatment of malignant gliomas with intramuscularly administered polyinosinic-polycytidylic acid stabilized with polylysine and carboxymethylcellulose: an open pilot study," Neurosurgery, 38(6): 1096-1104.
Salgaller et al., 1996, "Immunization against epitopes in the human melanoma antigen gplOO following patient immunization with synthetic peptides," Cancer Research, 56:4749-4757.
Sampson et al., 2009, "An epidermal growth factor receptor variant III-targeted vaccine is safe and immunogenic in patients with glioblastoma multiforme," Molecular Cancer Therapeutics, 8(10): 2773-2779.
Sarela et al., 2000, "Expression of the antiapoptosis gene, Survivin, predicts death from recurrent colorectal carcinoma", Gut J, 46(5):645-650.
Sarela et al., 2002, "Expression of survivin, a novel inhibitor of apoptosis and cell cycle regulatory protein, in pancreatic adenocarcinoma", British J Can, 86:886-892.
Sasaki et al., 2007, "Preferential Expression of Very Late Antigen-4 on Type 1 CTL Cells Plays a Critical Role in Trafficking into Central Nervous System Tumors," Cancer Research, 67(13): 6451-6458.
Satoh et al., 2001, "Expression of survivin is correlated with cancer cell apoptosis and is involved in the development of human pancreatic duct cell tumors", Cancer, 92(2):271-278.
Saudek et al., 1989, "A Preliminary Trial of the Programmable Implantable Medication System for Insulin Delivery," New England Journal of Medicine, 321(9): 574-579.
Scardino et al., 2002, "HER-2/neu and hTERT cryptic epitopes as novel targets for broad spectrum tumor immunotherapy," The Journal of immunology, 169:5900-5906.
Schnolzer et al., 1992, "Constructing proteins by dovetailing unprotected synthetic peptides: backbone-engineered HIV protease," Science, 256(5054): 221-225.
Schreier et al., 1986, "Allotypic differences in murine µ genes", Nucl Acids Res, 14:2381-2389.
Sefton et al., 1987, "Implantable pumps," CRC Critical Reviews in Biomedical Engineering, 14(3): 201-240.
Sherman et al., 1998, "Strategies for tumor elimination by cytotoxic T lymphocytes", Critical Reviews in Immunology, 18:47-54.
Shoji et al., 2008, "Plant-expressed HAas a seasonal influenza vaccine candidate," Vaccine, 26: 2930-2934.
Singh et al., 2003, "Identification of a cancer stem cell in human brain tumors", Cancer Res, 63:5821-5828.
Singh et al., 2004, "Cancer stem cells in nervous system tumors", Oncogene, 23:7267-7273.

(56) References Cited

OTHER PUBLICATIONS

Singh et al., 2004, "Identification of human brain tumor-initiating cells", Nature, 432:396-401.
Slingluff et al., 2008, "Helper T-cell responses and clinical activity of a melanoma vaccine with multiple peptides from MAGE and melanocytic differentiation antigens," Journal of Clinical Oncology, 26(30): 4973-4980.
Smith et al., 2001, "PTEN Mutation, EGFR amplification, and outcome in patients with anaplastic astrocytoma and glioblastoma multiforme," Journal of the National Cancer Institute, 93(16): 1246-1256.
Smith, 1994, "Cancer and the immune system", Clinical Immunology, 41(4):841-849.
Stoute et al., 1997, "A preliminary evaluation of a recombinant circumsporozoite protein vaccine against Plasmodium falciparum malaria," The New England Journal of Medicine, 336(2): 86-91.
Szczepanski et al., 2009, "Triggering of toll-like receptor 4 expressed on human head and neck squamous cell carcinoma promotes tumor development and protects the tumor from immune attack," Cancer Research, 69(7): 3105-3113.
Tam et al., 1979, "Improved synthesis of 4-(boc-aminoacyloxymethyl)-phenylacetic acids for use in solid phase peptide synthesis," Synthesis, 955-957.
Tam et al., 1995, "Specificity and formation of unusual amino acids of an amide ligation strategy for unprotected peptides," International Journal of Peptide & Protein Research, 45(3): 209-216.
Tanaka et al., 2000, "Expression of survivin and its relationship to loss of apoptosis in breast carcinomas", Clin Cancer Res, 6: 127-134.
Tarr, 1996, "Granulocyte-macrophage colony-stimulating factor and the immune system", Med Oncol., 13(3): 133-140.
Tatsumi et al., 2003, "Disease stage variation in CD4 and CD8 T-cell reactivity to the receptor tyrosine kinase EphA2 in patients with renal cell carcinoma", Cancer Research, 63:4481-4489.
Uematsu et al., 2005, "Prognostic significance of the immunohistochemical index of survivin in glioma: a comparative study with the MIB-1 index," Journal of Neuro-Oncology, 72: 231-238.
Van Heeke et al., 1989, "Expression of human asparagine synthetase in *Escherichia coli*," The Journal of Biological Chemistry, 264(10): 5503-5509.
Vescovi, A.L. et al., 2006, "Brain tumour stem cells," Nature Reviews Cancer, Nature Publishing Group, 6: 425-436.
Vredenburgh et al., 2007, "Bevacizumab plus irinotecan in recurrent glioblastoma multiforme," Journal of Clinical Oncology, 25(30): 4722-4729.
Vredenburgh et al., 2007, "Phase II trial of bevacizumab and Irinotecan in recurrent malignant glioma," Clinical Cancer Research, 13(4): 1253-1259.
Wallenfriedman et al., 1999, "Effects of continuous localized infusion of granulocyte—macrophage colony-stimulating factor and inoculations of irradiated glioma cells on tumor regression" J. Neurosurg 90: 1064-1074.
Watchmaker et al., 2010, "Independent regulation of chemokine responsiveness and cytolytic function versus CD8 + T cell expansion by dendritic cells," The Journal of Immunology, 184: 591-597.
Weber et al., 2008, "Phase 1 trial of Intranodal injection of a melan-NMART-1 DNA plasmid vaccine in patients with stage iv melanoma," J. Immunother., 31(2): 215-223.
Wen et al., 2004, "Malignant gliomas", Neurology and Neuroscience Reports, 4(3):218-227.
Wheeler et al., 2008, "Vaccination elicits correlated immune and clinical responses in glioblastoma multiforme patients," Cancer Research, 68(14): 5955-5964.
Wykosky et al., 2005, "EphA2 as a novel molecular marker and target in glioblastoma multiforme", Mol Can Res, 3(10):541-561.
Xiang et al., 2005, "A DNA Vaccine Targeting Survivin Combines Apoptosis with Suppression of Angiogenesis in Lung Tumor Eradication," Cancer Research 55: 553-561.

Yamanaka et al., 2005, "Clinical evaluation of dendritic cell vaccination for patients with recurrent glioma: results of a clinical phase 1/11 trial," Clinical Cancer Research, 11(11): 4160-4167.
Yamanaka et al., 2007, "Peptide-based immunotherapeutic approaches to glioma: a review", Expert Opinion Bio Ther, 7(5):645-649.
Yamashiro et al., 1988, "New segment synthesis of a-inhibin-92 by the acyl disulfide method," Int. J. Peptide Protein Res., 31(3): 322-334.
Yu et al., 2002, "Increased expression of survivin in gastric cancer patients and in first degree relatives", British J Can, 87:91-97.
Yu et al., 2004, "Vaccination with tumor lysate-pulsed dendritic cells elicits antigen-specific, cytotoxic T-cells in patients with malignant glioma", Cancer Research, 64(14):4973-4979.
Zelinski et al., 2001, "EphA2 overexpression causes tumorigenesis of mammary epithelial cells", Cancer Research, 61:2301-2306.
Ahmed et al., 1975, "Nonenzymic reactivation of reduced bovine pancreatic ribonuclease by air oxidation and by glutathione oxidoreduction buffers", The Journal of Biological Chemistry, 250(21):8477-8482.
Albericio et al., 1985, "Improved approach for anchoring Na-9-fluorenylmethyloxycarbonylamino acids ad p-alkoxybenzyl esters in solid-phase peptide synthesis", International Journal of Peptide and Protein Research, 26 (1 ):92-97.
Alexander et al., 1994, "Development of high potency universal DR-restricted helper epitopes by modification of high affinity DR-blocking peptides", Immunity, 1:751-761.
Alves et al., 2003, "EphA2 as target of anticancer immunotherapy: identification of HLA-A*0201-restricted epitopes", Cancer Research, 63:8476-8480.
Andersen et al., 2001, "spontaneous cytotoxic T-cell responses against survivin-derived mhc class I-restricted T-cell epitopes in situ as well as ex vivo in cancer patients", Cancer Res, 61:5964-5968.
Baca et al., 1995, "Chemical ligation of cysteine-containing peptides: synthesis of a 22 kDa tethered dimer of HIV-1 protease", J. Am. Chem. Soc. 117: 1881-1887.
Bakker et al., 1995, "Generation of antimelanoma cytotoxic t lymphocytes from healthy donors after presentation of melanoma-associated antigen-derived epitopes by dendritic cells in vitro", Cancer Research, 55:5330-5334.
Bedrosian et al., 2003, "Intranodal administration of peptide-pulsed mature dendritic cell vaccines results in superior CDS+ T-cell function in melanoma patients," Journal of Clinical Oncology, 21 (20): 3826-3835.
Bernatchez et al., 2011, "Altered decamer and nonamer from an HLA-A0201-restricted epitope of Survivin differentially stimulate T-cell responses in different individuals", Vaccine, 29(16):3021-3030.
Berzofsky, 2004, "New strategies for designing and optimizing vaccines", ASM News, 70(5):219-223.
Bigg et al., 2006, The mammalian chitinase-like lectin, YKL-40, binds specifically to type I collagen and modulates the rate of type I collagen fibril formation, The Journal of Biological Chemistry, 281(30): 21081-21095.
Bigner et al., 1981, "Induction of lethal experimental allergic encephalomyelitis in nonhuman primates and guinea pigs with human glioblastoma multiforme tissue", Journal of Neurosurgery, 55:32-42.
Binda et al, 2012, "The EphA2 Receptor Drives Self-Renewal and Tumorigenicity in Stem-like Tumor-Propagating Cells from Human Glioblastomas," ECancer Cell; vol. 22, pp. 765-780.
Bitter et al., 1987, "Expression and secretion vectors for yeast," methods in enzymology, Recombinant DNA, 153 (Part D): 516-544.
Blanc-Brude et al., 2002, "Inhibitor of apoptosis protein survivin regulates vascular injury," Nature Medicine, 8(9): 987-994.
Bonnet et al., 1997, "Human acute myeloid leukemia is organized as a hierarchy that originates from a primitive hematopoietic cell", Nat Med, 3: 730-737.
Boon, 1992, "Towards a genetic analysis of tumor rejection antigens", Advance Cancer Research, 58:177-210.
Bork, 2000, "Powers and Pitfalls in Sequence Analysis: The 70% Hurdle," Genome Research 10:398-400.

(56) References Cited

OTHER PUBLICATIONS

Bowie et al., 1990, "Deciphering the Message in Protein Sequences: Tolerance to Amino Acid Substitutions," Science 247, pp. 1306-1310.

Bownds et al., 2001, "Induction of Tumor-Reactive Cytotoxic T-Lymphocytes Using a Peptide from NY-ES0-1 Modified at the Carboxy-terminus to Enhance HLA-A2.I Binding Affinity and Stability in Solution", Journal of immunotherapy, 24(1): 1-9.

Brantley et al., 2002, "Soluble Eph A receptors inhibit tumor angiogenesis and progression in vivo", Ocogene, 21(46):7011-7026.

Brown et al., 2012, "Stem-like Tumor Initiating Cells Isolated from IL 13Ra2 Expressing Gliomas Are Targeted and Killed by IL 13-Zetakine-Redirected T Cells," Clinical Cancer Research, 18(8): 2199-2209.

Buchwald et al., 1980, "Long-term, continuous intravenous heparin administration by an implantable infusion pump in ambulatory patients with recurrent venous thrombosis," Surgery, 88(4): 507-516.

Burgess et al., 1990, "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol. 111:2129-2138.

Butowski et al., 2009, "A North American brain tumor consortium phase II study of poly-ICLC for adult patients with recurrent anaplastic gliomas," J. Neurooncol., 91: 183-189.

Butowski et al., 2009, "A phase II clinical trial of poly-ICLC with radiation for adult patients with newly diagnosed supratentorial glioblastoma: a North American Brain Tumor Consortium (NABTCO 1-05)," J. Neurooncol., 91: 175-182.

Byers, 1999, "What can randomizing controlled trials tell us about nutrition and cancer prevention" CA Journal, 49(6):353-361.

Carmon et al., 2002, "Characterization of novel breast carcinoma-associated BA46-derived peptides in HLA-A2.I/D (b)-beta2m transgenic mice", The Journal of Clinical Investigation, 110(4):453-462.

Celis, 2007, "Overlapping human leukocyte antigen class 1/11 binding peptide vaccine for the treatment of patients with stage IV melanoma: Evidence of systemic immune dysfunction", Cancer, 110:203-214.

Chen et al., 2000, "Identification of NY-ES0-1 peptide analogues capable of improved stimulation of tumor-reactive CTL," The Journal of immunology, 165(2): 948-955.

Chianese-Bullock et al., 2005, "MAGE-A1-, MAGE-A10, and gp100-derived peptides are immunogenic when combined with granulocyte-macrophage colony-stimulating factor and Montanide ISA-51 adjuvant and administered as part of a multi peptide vaccine for melanoma," The Journal of Immunology, 174(5): 3080-3086.

Ciesielski et al., 2006, "Antitumor effects of a xenogeneic survivin bone marrow derived dendritic cell vaccine against murine GL261 gliomas," Cancer Immunol Immunother 55: 1491-1503.

Ciesielski et al., 2010, "Antitumor cytotoxic T-cell response induced by a survivin peptide mimic," Cancer Immunol. Immunother., 59: 1211-1221.

Cockett et al., 1990, "High Level Expression of Tissue Inhibitor or Metalloproteinases in Chinese Hamster Ovary Cells Using Glutamine Synthetase Gene Amplification," BioTechnology, 8(7): 662-667.

Cohen et al., 2003, "Survivin expression in ovarian carcinoma: correlation with apoptotic markers and prognosis", Modem Pathology, 16:574-583.

Cohen et al., 2009, "FDA drug approval summary: bevacizumab (Avastin®) as treatment of recurrent glioblastoma multiforme," The Oncologist, 14: 1131-113 8.

Colbere-Garapin et al., 1981, "A new dominant hybrid selective marker for higher eukaryotic cells," J. Mol. Biol., 150: 1-14.

Correction, 2006, Clinical Cancer Research, 12(11): 3552.

Cotterchio et al., 2000, "Ontario familial colon cancer registry: methods and firstyear response rates," Chronic Diseases in Canada, 21(2): 1-10.

Crouse et al., 1983, "Expression and amplification of engineered mouse dihydrofolate reductase minigenes," Molecular and Cellular Bioliogy, 3(2): 257-266.

Daines et al., 2002, "A Novel Mechanism by Which Interferon-y Can Regulate Interleukin (IL)-13 Responses," J. Biol. Chem., 277(12): 10387-10393.

D'Aoust et al., 2008, "Influenza virus-like particles produced by transient expression in Nicotiana benthamiana induce a protective immune response against a lethal viral challenge in mice," Plant Biotechnology Journal, 6: 930-940.

De Vleeschouwer et al., 2008, "Postoperative adjuvant dendritic cell- based immunotherapy in patients with relapsed glioblastoma multiforme," Clinical Cancer Research, 14(10): 3098-3104.

Debinski and Gibo, 2000, "Molecular expression analysis of restrictive receptor for interleukin 13, a brain tumor-associated cancer/testis antigen", Molecular Medicine, 6(5):440-449.

Debinski et al., 1999, "Receptor for Interleukin 13 is a marker and therapeutic target for human high-grade gliomas," Clinical Cancer Research, 5: 985-990.

Debinski et al., 1999, "Receptor for interleukin 13 is abundantly and specifically over-expressed in patients with glioblastoma multiforme", International Journal of Oncology, 15:481-486.

Debinski et al., 2000, "Expression of a restrictive receptor for interleukin 13 is associated with glial transformation", Journal ofNeuro-Oncology, 48: 103-111.

Debinski et al., 2004, EphA2 receptor represents a new marker and therapeutic target in glioblastoma multiforme (GMB), Neuro-Oncology, Abstract GE02, oo.308, 336-337.

Dhodapkar et al., 2011, "Vaccines targeting cancer stem cells", The Cancer Journal, 17(5):397-402.

Dorland's Illustrated Medical Dictionary, 2007, "Vaccine".

Zhang et al., 2007, "Antigenic profiling of glioma cells to generate allogeneic vaccines or dendritic cell-based therapeutics", Clin Cancer Res, 13(2):566-575.

Zhu et al., 2007, "Toll like receptor-3 ligand poly-ICLC promotes the efficacy of peripheral vaccinations with tumor antigen-derived peptide epitopes in murine CNS tumor models," Journal of Translational Medicine, 5(10): 1-15.

Zhu et al., 2010, "Poly-ICLC promotes the infiltration of effector T cells into intracranial gliomas via induction ofCXCL 10 in IFN-a and IFN-y dependent manners," Cancer Immunol. Immunother. 59: 1401-1409.

"Immune System Modulators," National Cancer Institute (Sep. 24, 2019), available at https://www.cancer.gov/about-cancer/treatment/types/immunotherapy/immune-system-modulators.

Bascones-Martinez et al., "Immunomodulatory drugs: oral and systemic adverse effects," Med Oral Patol Oral Cir Bucal. 19(1):e24-e31 (Aug. 29, 2013).

Shah et al., "T cell receptor (TCR) signaling in health and disease," Signal Transduction and Targeted Therapy 6:412 (2021), 26 pages.

\* cited by examiner

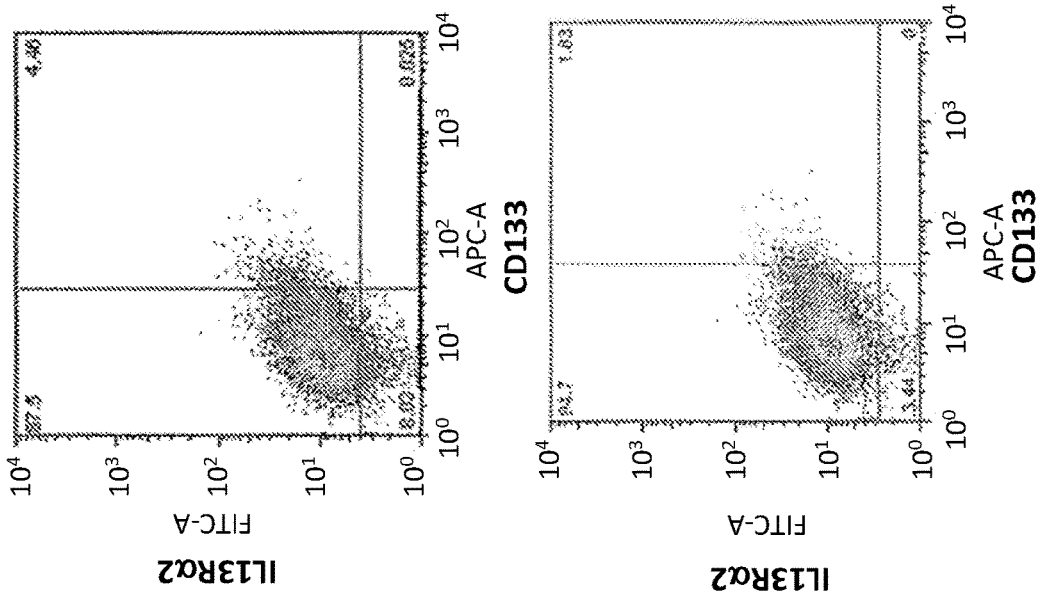
*Fig. 3B*  *Fig. 3A*
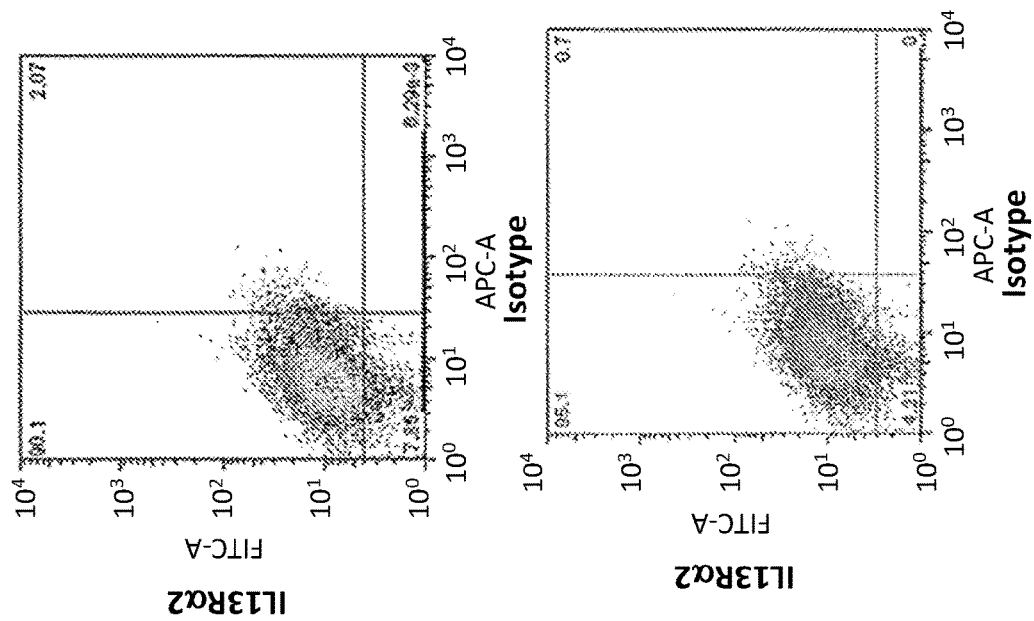
*Fig. 3D*  *Fig. 3C*

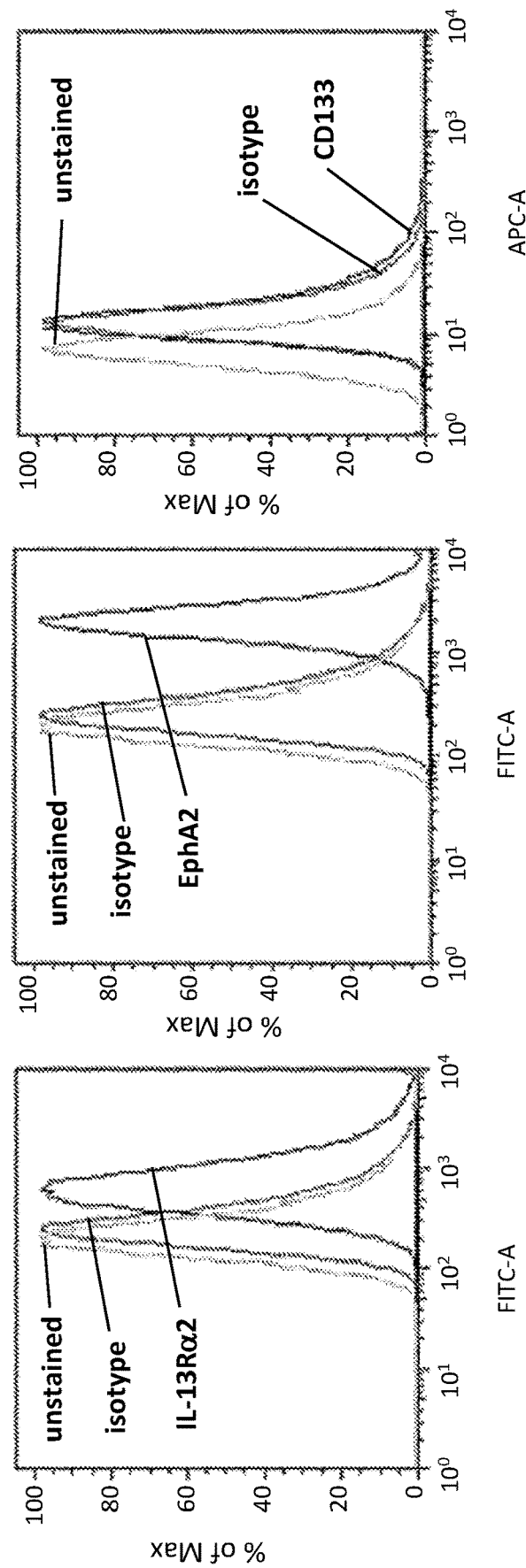
*Fig. 6A* *Fig. 6B* *Fig. 6C*

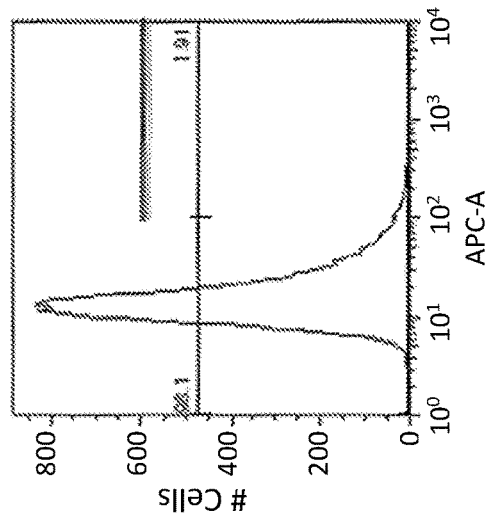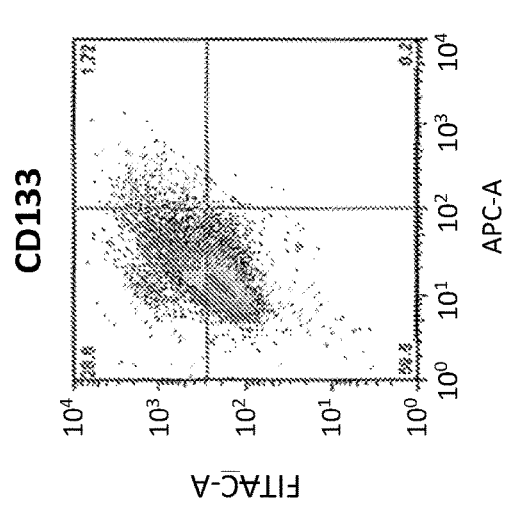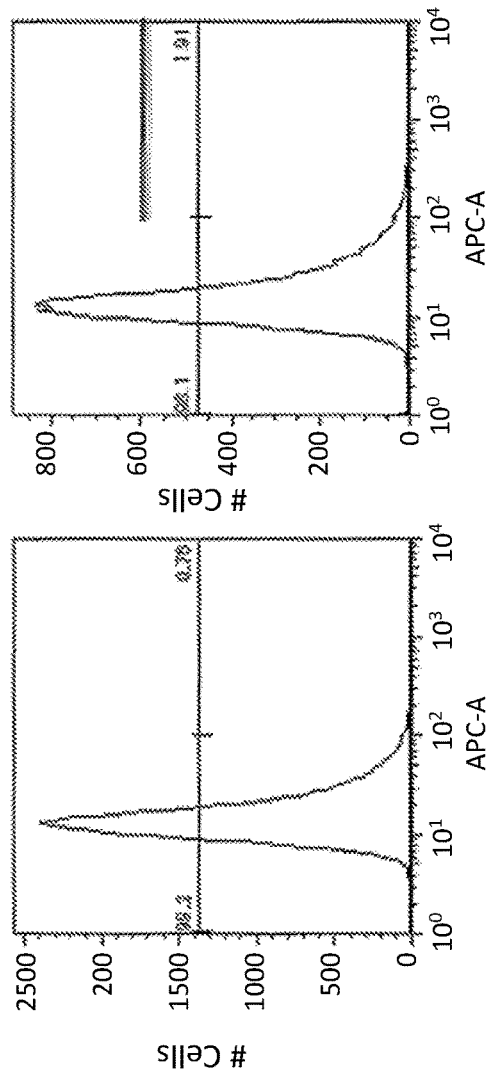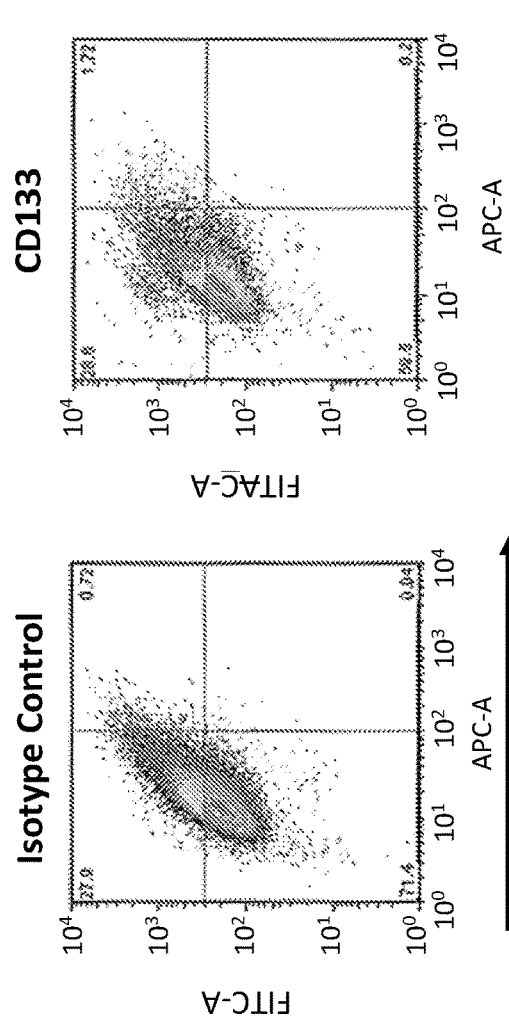

CANCER STEM CELL TARGETED CANCER VACCINES

CROSS-REFERENCE TO RELATED APPLICATIONS

The present application is a continuation of U.S. application Ser. No. 16/599,031, filed Oct. 10, 2019, which is a continuation of U.S. application Ser. No. 14/401,053, filed Nov. 13, 2014, which issued as U.S. Pat. No. 10,485,858, which is a 371 National Stage of U.S. Application No. PCT/US2013/41063, filed May 15, 2013, which claims the benefit of priority to U.S. Provisional Patent Application No. 61/647,615, filed May 16, 2012, the disclosures of each of which are herein incorporated by reference in their entireties.

SEQUENCE LISTING

This patent application is filed with a sequence listing in electronic format. The Sequence Listing is provided as a file entitled "2023-04-27_01214-0010-02US_ST26.xml," which was created on Apr. 27, 2023, and which is 13,697 bytes in size. The information in the electronic format of the sequence listing is incorporated herein by reference in its entirety.

INTRODUCTION

Provided herein are peptide-based cancer stem cell targeted vaccines and methods for treating and vaccinating against cancer comprising administering to patients in need thereof cancer stem cell targeted vaccines. In a preferred embodiment, the vaccine is administered to patient with brain cancer. Also provided herein are vaccine regimens that include doses and schedules of administration of the vaccine. Also provided herein are components of the cancer stem cell targeted vaccine that are combined or administered as a component of the regimen, such as peptides derived from cancer antigens, helper peptides, adjuvants, emulsifiers and/or immunostimulants. Also provided are patient populations to which the cancer vaccine can be administered. The cancer stem cell targeted vaccines of the present invention also target tumor bulk cells (the non-cancer stem cells of the tumor).

BACKGROUND

Cancer is one of the most significant health conditions. The American Cancer Society's Cancer Facts and Figures, 2003, predicts over 1.3 million Americans will receive a cancer diagnosis this year. In the United States, cancer is second only to heart disease in mortality accounting for one of four deaths. In 2002, the National Institutes of Health estimated total costs of cancer totaled $171.6 billion, with $61 billion in direct expenditures. The incidence of cancer is widely expected to increase as the US population ages, further augmenting the impact of this condition. The current treatment regimens for cancer, established in the 1970s and 1980s, have not changed dramatically. These treatments, which include chemotherapy, radiation and other modalities including newer targeted therapies, have shown limited overall survival benefit when utilized in most advanced stage common cancers since, among other things, these therapies primarily target tumor bulk rather than cancer stem cells.

More specifically, conventional cancer diagnosis and therapies to date have attempted to selectively detect and eradicate neoplastic cells that are largely fast-growing (i.e., cells that form the tumor bulk). Standard oncology regimens have often been largely designed to administer the highest dose of irradiation or a chemotherapeutic agent without undue toxicity, i.e., often referred to as the "maximum tolerated dose" (MTD) or "no observed adverse effect level" (NOAEL). Many conventional cancer chemotherapies (e.g., alkylating agents such as cyclophosphamide, antimetabolites such as 5-Fluorouracil, plant alkaloids such as vincristine) and conventional irradiation therapies exert their toxic effects on cancer cells largely by interfering with cellular mechanisms involved in cell growth and DNA replication. Chemotherapy protocols also often involve administration of a combination of chemotherapeutic agents in an attempt to increase the efficacy of treatment. Despite the availability of a large variety of chemotherapeutic agents, these therapies have many drawbacks (see, e.g., Stockdale, 1998, "Principles Of Cancer Patient Management" in Scientific American Medicine, vol. 3, Rubenstein and Federman, eds., ch. 12, sect. X). For example, chemotherapeutic agents are notoriously toxic due to non-specific side effects on fast-growing cells whether normal or malignant; e.g. chemotherapeutic agents cause significant, and often dangerous, side effects, including bone marrow depression, immunosuppression, gastrointestinal distress, etc.

Cancer stem cells comprise a unique subpopulation (often 0.1-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e. those cancer cells that comprise the tumor bulk), cancer stem cells which are often slow-growing may be relatively more resistant than faster growing tumor bulk to conventional therapies and regimens. Cancer stem cells can express other features which make them relatively chemoresistant such as multi-drug resistance and anti-apoptotic pathways. The aforementioned would constitute a key reason for the failure of standard oncology treatment regimens to ensure long-term benefit in most patients with advanced stage cancers—i.e. the failure to adequately target and eradicate cancer stem cells. In some instances, a cancer stem cell(s) is the founder cell of a tumor (i.e., it is the progenitor of the cancer cells that comprise the tumor bulk).

Cancer stem cells have been identified in a large variety of cancer types. For instance, Bonnet et al., using flow cytometry were able to isolate the leukemia cells bearing the specific phenotype CD34+CD38−, and subsequently demonstrate that it is these cells (comprising <1% of a given leukemia), unlike the remaining 99+% of the leukemia bulk, that are able to recapitulate the leukemia from which it was derived when transferred into immunodeficient mice. See, e.g., "Human acute myeloid leukemia is organized as a hierarchy that originates from a primitive hematopoietic cell," Nat Med 3:730-737 (1997). That is, these cancer stem cells were found as <1 in 10,000 leukemia cells yet this low frequency population was able to initiate and serially transfer a human leukemia into severe combined immunodeficiency/non-obese diabetic (NOD/SCID) mice with the same histologic phenotype as in the original tumor.

Brain cancer is an attractive tumor type in which to target cancer stem cells with immunotherapy. Kondo et al. isolated a small population of cells from a C6-glioma cell line, which was identified as the cancer stem cell population by virtue of its ability to self-renew and recapitulate gliomas in immunocompromised mice. See Kondo et al., "Persistence of a small population of cancer stem-like cells in the C6 glioma cell line," Proc. Natl. Acad. Sci. USA 101:781-786 (2004). In this study, Kondo et al. determined that cancer cell lines contain a population of cancer stem cells that confer the ability of the line to engraft immunodeficient mice. Singh et al. identified brain tumor stem cells. When isolated and transplanted into nude mice, the CD133+ cancer stem cells, unlike the CD133– tumor bulk cells, form tumors that can then be serially transplanted. See Singh et al., "Identification of human brain tumor initiating cells," Nature 432:396-401 (2004); Singh et al., "Cancer stem cells in nervous system tumors," Oncogene 23:7267-7273 (2004); Singh et al., "Identification of a cancer stem cell in human brain tumors," Cancer Res. 63:5821-5828 (2003).

Immunotherapy is a promising new approach in the treatment of cancer, which will serve to activate the immune system to target and kill tumor cells with less toxicity than standard cancer treatments, and provide durable responses and prolonged survival through the immunosurveillance the tumors via memory T cells. The efficacy of peripheral immunizations with autologous cells or dendritic cells (DC) pulsed with synthetic peptides for tumor-antigen-specific T cell epitopes has been demonstrated Such antigen-specific approaches may be effective because presentation of immunogenic T cell-epitopes and stimulation of antigen-specific T cell precursors can take place efficiently with the use of specific antigen-peptides. The immune system has the unique potential to mobilize responses that are highly specific to protein antigens. To this end, cancer vaccines are designed to stimulate the immune system to specifically recognize and attack antigens expressed by cancer cells. The cells of the immune system that provide this targeted protection are called lymphocytes. In particular, cytotoxic T cells (also called CD4+ T cells) have the ability to specifically kill cancer cells that express the cancer antigen recognized by these immune cells.

Cancer vaccines are designed to activate cytotoxic T cells and direct them to recognize and attack cancer cells. Cancer vaccines, which can be comprised of tumor lysate, a single epitope, or multiple epitopes, can be administered to a patient in a variety of ways, including via 1) harvested autologous Daces that are exposed to antigen peptides ex vivo and then reintroduced back into the patient (e.g. via intranasal injection), or 2) direct injection of the antigen peptides into a patient (e.g. subcutaneously).

GM-CSF enhances the immune response to tumor antigens through a variety of mechanisms. GM-CSF increases the cytotoxic activity of CD8+ T cells (see, e.g., Tarr, Med Oncol, 1996). GM-CSF also induces the migration and maturation of antigen-presenting cells, including dendritic cells (DCs), which are critical to the activation of cytotoxic T-cells. GM-CSF also polarizes the immune response toward the Th1 phenotype, which is optimal for a robust anti-tumor response.

IL-13Rα2 is known to be expressed in a broad spectrum of cancer types, but not in normal tissues (Debinski et al., 2000). IL-13Ra2 is expressed in brain, mesothelioma, esophageal, Hodgkin's disease, prostate, breast and colon cancer.(Debinski and Gibo, Mol Med, 2000; Wykosky et al. Mol Can Res 2005; Wykosky et al. Clin Can Res 2003; Wykosky et al. Mol Can Res 2007). An HLA (human leukocyte antigen)-A2-restricted cytotoxic T lymphocyte (CTL) epitope derived from the interleukin (IL)-13 receptor (R) α2 was recently identified (Okano et al., 2002), thus making the identified epitope (IL-13Rα2$_{345-353}$) an attractive component of peptide-based vaccines for gliomas. By generating unique CTL lines by stimulation of CD8+ cells with the peptide IL-13Rα2$_{345-353}$, it was demonstrated that IL-13Ra2 positive, HLA-A2 positive glioma cells were efficiently lysed in an antigen-specific manner. Eguchi et al. (2006) identified a mutant peptide of the IL-13Rα2$_{345-353}$, with two amino acid substitutions that increased the affinity for HLA-A2 and produced a more robust T cell response (i.e., was more immunogenic) than the wild type peptide. To create this peptide, Okano et al substituted the amino acid at position 1 with alanine, and the amino acid at position 9 with valine. The resulting mutant peptide is called IL-13Rα2$_{345-353:1A9V}$. T cells stimulated with the mutant peptide were more effective at killing glioma cells than T cells stimulated with the wild type. As such, the mutant peptide is an attractive component of a brain cancer vaccine.

EphA2 is a member of the Eph family of receptor tyrosine kinases, comprised of two major classes (EphA2 and EphB), which are distinguished by their specificities for ligands (ephrin-A and ephrin-B, respectively). EphA2 is frequently overexpressed and often functionally dysregulated in advanced cancers, as well as metastatic lesions (Kinch et al., 2003). Due to the aggressive and invasive nature of malignant gliomas, EphA2 might be expressed in this tumor entity and could be a potential target for glioma vaccines. EphA2 is also expressed in brain, breast, prostate, lung and colon cancers (Debinski and Gibo, Mol Med, 2000; Wykosky et al. Mol Can Res 2005; Wykosky et al. Clin Can Res 2003; Wykosky et al. Mol Can Res 2007). T-cell immunoepitopes in EphA2 have been identified and characterized as potential targets and surrogate markers for other forms of cancer immunotherapy (Alves et al., 2003, and Tatsumi et al., 2003).

Survivin is an apoptosis inhibitor protein that is overexpressed in most human cancers, and inhibition of its function results in increased apoptosis (see, e.g., Blanc-Brude et al., Nat. Med., 8: 987-994, 2002). Expression of survivin has been demonstrated in lung, esophageal, breast, pancreatic, ovarian, melanoma, colorectal, hepatocellular, gastric, and bladder cancers, as well as in a variety of hematologic malignancies including acute myelogenous leukemia (AML) and acute lymphocytic leukemia (ALL). (Li et al. Can Res 1999; Grabowski et al. Br J Can 2003; Tanaka et al. Clin Can Res 2000; Nasu et al. Antican Res 2002; Satoh et al. Cancer 2001; Sarela et al. Br J Can 2002; Cohen et al. Mod path 2003; Naor et al. Am J Dermatopath 2008; Sarela et al. Gut 2000; Ikeguchi et al. Diagn Mol Pathol 2002; Ito et al. Hepatopathology 2000; Yu et al. Br J Can 2002; Lu et al. Cancer Res 1998; Lehner et al. Appl Immunohis Mol Morphol 2002; Mori et al. Int J Hematol 2002). This expression pattern makes survivin an attractive cancer vaccine target. Survivin has also been shown to be expressed on cancer stem cells in a variety of cancers, including glioblastoma, renal cancer, prostate cancer and colon cancer (Liu et al. Molecular Cancer 5(67):2006; Nishizawa et al. Cancer Res 2012; Liao et al. Cancer Res 70(18): 2010. In a separate study, Andersen et al. (Cancer Research 61:2001) identified a series of T cell epitopes from survivin that were recognized by the peripheral T cells of cancer patients. Moreover, Andersen et al. identified analogs of these peptides by making substitutions in the amino acids of the peptides, that were more immunogenic than the wild type peptides, and activated T cells that were cytotoxic to cancer cells. In addition, Bernatchez et al (Vaccine 29(16): 2011) identified additional survivin analog peptides that were also immunogenic (including SEQ ID NO:9 presented herein), and able to activate T cells that were cytotoxic to cancer cells.

The cancer stem cell targeted vaccines of the present invention also target tumor bulk cells (the non-cancer stem cells of the tumor) in that they may contain peptides from tumor associated antigens that are expressed by both the cancer stem cells as well as the tumor bulk cells. Therefore, as used herein, the term "cancer stem cell targeted vaccine" and "cancer vaccine" are used interchangeably.

SUMMARY

Provided herein are cancer stem cell targeted cancer vaccines and the components, dosages, routes of administration, schedules, and regimens, as well as the patient populations to which they can be administered. Included herein among the components that comprise the vaccine are tumor associated antigens and cancer stem cell associated antigens, and peptides derived from these antigens, as well as immunomodulatory agents (also known as adjuvants), and emulsifiers, and the combinations of these components, to be administered.

The present invention is a multiple epitope vaccine in which the epitopes are derived from tumor antigens. The epitope peptides are injected subcutaneously (for example) and enter the draining peripheral lymph nodes (e.g. the maxillary or inguinal nodes). Daces then "display" the peptides on their cell surface, via a process called antigen presentation. Cytotoxic T cells systematically interact with Daces in the lymph node, and are activated upon binding to Daces that "present" the peptides. This process results in the activation and expansion of the antigen specific cytotoxic T cells, and also "arms" the T cells so they have the capacity to kill cancer cells. Additional compounds, called immunoadjuvants, can be administered in combination with cancer vaccines in order to enhance the environment for immunity. GM-CSF is one such immunomodulatory agent which has been shown to be efficacious when used with cancer vaccines. Imiquimod is another such immunomodulatory agent which has been shown to be efficacious when used with cancer vaccines.

In one aspect, provided herein is a peptide derived from IL-13Rα2, which serves as a HLA-A2-restricted cytotoxic T lymphocyte (CTL) epitope. The IL-13Rα2 peptide can comprise, consist of, or consist essentially of a substitution mutant variant of WLPGFILI (SEQ ID NO:1), wherein at least one of the amino acid residues can be substituted for an amino acid other than the indicated residue. In addition, the IL-13Rα2 peptide can comprise, consist of, or consist essentially of any of the following sequences: WLPFGFILV (SEQ ID NO:2), ALPFGFILV (SEQ ID NO:3), or ELPFGFILV (SEQ ID NO:4). In a preferred embodiment, the cancer stem cell targeted cancer vaccine includes the peptide corresponding to SEQ ID NO:4. In one aspect, provided herein are peptides derived from survivin, which serve as HLA-A2-restricted cytotoxic T lymphocyte (CTL) epitopes. The survivin peptides can comprise, consist of, or consist essentially of a substitution mutant variant of LTLGEFLKL (SEQ ID NO:6) or a substitution mutant of ELTLGEFLKL (SEQ ID NO:8), wherein at least one of the amino acid residues can be substituted for an amino acid other than the indicated residue. In addition, the survivin peptide can comprise, consist of, or consist essentially of any of the following sequences: LMLGEFLKL (SEQ ID NO:7), ELMLG EFLKL (SEQ ID NO:9). In a preferred embodiment, the cancer stem cell targeted cancer vaccine includes the peptide corresponding to SEQ ID NO:7. In another preferred embodiment, the cancer stem cell targeted cancer vaccine includes the peptide corresponding to SEQ ID NO:9. In another preferred embodiment, the cancer stem cell targeted cancer vaccine includes both of the peptides corresponding to SEQ ID NO:7 and SEQ ID NO:9.

Also provided herein is a use of any of the above IL-13Rα2 peptides as a cancer stem cell targeted cancer vaccine. In addition, the invention provides a method of vaccinating a patient against cancer, where the peptide is introduced into a patient under conditions sufficient for the patient to develop a CTL response. Further, provided herein is a use of an EphA2 peptide having the sequence TLADFDPRV (SEQ ID NO:5) or a composition comprising said peptide and a physiologically acceptable carrier, as a vaccine for glioma. Also provided herein is a method of vaccinating a patient against glioma, wherein an EphA2 peptide having the sequence TLADFDPRV (SEQ ID NO:5) or a composition comprising said peptide and a physiologically acceptable carrier, is introduced into a patient under conditions sufficient for the patient to develop a CTL response.

In another aspect, presented herein are cancer vaccines comprising an IL-13Rα2 peptide and one, two, three, or more additional cancer-associated peptides. In certain embodiments, the cancer vaccines described herein are administered concurrently with one or more helper T cell epitopes and/or one or more immunomodulatory agents. In accordance with such embodiments, the one or more helper T cell epitopes and/or one or more immunomodulatory agents may be administered as part of the vaccine (e.g., in solution with the IL-13Rα2 peptide and the one, two, three, or more additional brain cancer-associated peptides) or separate from the vaccine (i.e., the helper T cell epitopes and/or immune response modifiers may be administered as a formulation that is not a part of the vaccine formulation). In some embodiments, the cancer vaccines described herein are administered as cell-free vaccines. In another embodiment, the cancer vaccine is administered with an adjuvant. In another embodiment, the cancer vaccine is administered with an immunomodulatory agent. In a preferred embodiment, the cancer vaccine is administered in combination with additional peptides. In another embodiment, the peptides that comprise the cancer vaccine are administered with an emulsifier. In another embodiment, the peptides that comprise the cancer vaccine are administered as an emulsion in Montanide ISA 51, as a component of a regimen that includes injections with one or two immunomodulatory agents. (Montanide ISA 51 is an emulsifier that also is known to function in certain instances as an adjuvant.) In other embodiments, the cancer vaccines described herein are administered as dendritic cell vaccines.

In one embodiment, a cancer vaccine comprises an IL-13Rα2 peptide, an EphA2 peptide, and at least one survivin peptide. In a specific embodiment, a cancer vaccine comprises the IL-13Rα2 peptide corresponding to any one of SEQ ID NOs:1-4, the EphA2 peptide corresponding to SEQ ID NO:5, and the survivin peptide corresponding to any one of SEQ ID NOs:6-9. In specific preferred embodiment, a cancer vaccine comprises the IL-13Rα2 peptide corresponding to SEQ ID NO:3, the EphA2 peptide corresponding to SEQ ID NO:5, and one or both survivin peptides corresponding to SEQ ID NO:7 and SEQ ID NO:9. In some embodiments, the cancer vaccine is administered concurrently with one or more helper T cell epitopes. In a specific embodiment, the cancer vaccine is administered concurrently with a helper T cell epitope, wherein the helper T cell epitope is derived from tetanus toxoid. In a specific embodiment, the cancer vaccine comprises the Tetanus toxoid peptide corresponding to the sequence AQYIKANSKFIGI- TEL (SEQ ID NO:10). In some embodiments, the cancer vaccine is administered concurrently with one or more immune response modifiers. In a specific embodiment, one of the immune response modifiers is a TLR3 agonist. In another specific embodiment, the immune response modifier is imiquimod. In another specific embodiment, one of the immune response modifiers is GM-CSF. In another specific embodiment, the cancer vaccine regimen comprises both imiquimod and GM-CSF. In some embodiments, the cancer vaccine is a cell-free vaccine. In other embodiments, the cancer vaccine is a dendritic cell vaccine.

In another embodiment, a cancer vaccine comprises an IL-13Rα2 peptide, an EphA2 peptide, and at least one survivin peptide. In another embodiment, the cancer vaccine comprises two survivin peptides. In a specific embodiment, a cancer vaccine comprises the IL-13Rα2 peptide corresponding to any one of SEQ ID NOs:1-4, the EphA2 peptide corresponding to SEQ ID NO:5, at least one survivin peptide corresponding to SEQ ID NOs:6-9. In specific preferred embodiment, a cancer vaccine comprises the IL-13Rα2 peptide corresponding to SEQ ID NO:3, the EphA2 peptide corresponding to SEQ ID NO:5, one or both of the survivin peptides corresponding to SEQ ID NO:7 and SEQ ID NO:9. In some embodiments, the cancer vaccine is administered concurrently with one or more helper T cell epitopes. In a specific embodiment, the cancer vaccine is administered concurrently with a helper T cell epitope, wherein the helper T cell epitope is the Tetanus toxoid corresponding to SEQ ID NO:10. In some embodiments, the cancer vaccine is administered concurrently with one or more immune response modifiers. In a specific embodiment, peptides that comprise the cancer vaccine are administered to the patient as an emulsion by mixing with an emulsifier. In a specific embodiment, the emulsifier is Montanide ISA-51. In some embodiments, the cancer vaccine is a cell-free vaccine. In other embodiments, the cancer vaccine is a dendritic cell vaccine.

In a preferred embodiment, the immunomodulatory agent is granulocyte-macrophage colony stimulating factor, also known as GM-CSF (Leukine®; sargramostin; molgramostim; Leucomax®). GM-CSF enhances the immune response to tumor antigens through a variety of mechanisms. GM-CSF increases the cytotoxic activity of CD8+ T cells [Tarr, *Med Oncol*, 1996]. GM-CSF also induces the migration and maturation of antigen-presenting cells, including dendritic cells (DCs), which are critical to the activation of cytotoxic T-cells. GM-CSF also polarizes the immune response toward the Th1 phenotype, which is optimal for a robust anti-tumor response. In another preferred embodiment, GM-CSF is administered subcutaneously at a dose of 125 ug per injection. In another preferred embodiment, GM-CSF is administered subcutaneously at a dose of 100 ug per injection. In another preferred embodiment, the GM-CSF is administered in close proximity to the peptide injection. In another preferred embodiment, GM-CSF is administered within 3 centimeters of the peptide injection. In another preferred embodiment, the peptide injection is administered, and within 15 minutes the GM-CSF injection is then administered. In a preferred embodiment, the injections are administered every 3 weeks.

In a preferred embodiment, the peptide emulsion consists of a mixture of an aqueous solution (800 µl) containing three HLA-A2-restricted peptides (600 µg each of EphA2 (SEQ ID NO:5), IL-13Rα2 (SEQ ID NO:3), and one or both of the Survivin peptides (SEQ ID NO:7 and SEQ ID NO:9) and 800 µl containing 400 ug of the helper T cell peptide, (SEQ ID NO: 10), mixed at a 1:1 (volume/volume) ratio with the emulsifier, Montanide ISA-51. The final emulsion will have a total volume of 1.6 ml. The total volume to be administered to the patient is 800 µl. In this preferred embodiment, 300 µg of each tumor antigen derived peptide and 200 µg of the tetanus toxoid peptide are administered in each subcutaneous injection.

In a preferred embodiment, the cancer stem cell targeted cancer vaccine regimen consists of the emulsion delivered subcutaneously and, a separate subcutaneous injection of GM-CSF (referred to herein collectively as "the subcutaneous injections"). In another preferred embodiment, the cancer stem cell targeted cancer vaccine regimen consists of the emulsion delivered subcutaneously and, a separate subcutaneous injection of GM-CSF, and also comprises topical administration of imiquimod over both the site of the emulsion injection and the site of the GM-CSF injection. In a preferred embodiment, the topical imiquimod is administered on the same day as the subcutaneous injections. In another preferred embodiment, the topical imiquimod is administered on the same day as the subcutaneous injections, and is administered again 72 hours after the subcutaneous injections. In a preferred embodiment, the amount of imiquimod that is applied topically over the sites of the subcutaneous injections is

DEFINITIONS

As used herein, the terms "about" or "approximately" when used in conjunction with a number refers to any number within 1, 5 or 10% of the referenced number.

As used herein, the term "agent" refers to any molecule, compound, and/or substance that can be used in or in combination with an interleukin-13 receptor α2 peptide-based brain cancer vaccines described herein. The term agent includes, without limitation, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents, anti-angiogenic agents, and small molecule drugs.

As used herein, the term "amino acid sequence identity" refers to the degree of identity or similarity between a pair of aligned amino acid sequences, usually expressed as a percentage. As used herein, the terms "percent identity," "percent identical," "% identity," and "% identical" with respect to amino acid sequence refer to the percentage of amino acid residues in a candidate sequence that are identical (i.e., the amino acid residues at a given position in the alignment are the same residue) to the corresponding amino acid residue in the peptide after aligning the sequences and introducing gaps, if necessary, to achieve the maximum percent sequence homology. As used herein, the terms "percent similarity," "percent similar," "% similarity," and "% similar" with respect to amino acid sequence refer to the percentage of amino acid residues in a candidate sequence that are similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, including computer algorithms designed for this purpose, using the default parameters of said computer algorithms or the software packages containing them.

As used herein, the term "conservative substitution" refers to replacement of an amino acid of one class with another amino acid of the same class. In particular embodiments, a conservative substitution does not alter the structure or function, or both, of a peptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As used herein, "imiquimod" refers to an immunomodulatory agent (also known as an adjuvant) that binds to toll-like receptor 7 (TLR7). Imiquimod is also known by the commercial names Aldara®, Zyclara®, and Beselna®.

As used herein, "GM-CSF" refers to granulocyte-macrophage colony stimulating factor, which is referred to herein interchangeably as an adjuvant and as an immunomodulatory agent. Brand and generic names for GM-CSF include Leukine®, sargramostin, molgramostim, and Leucomax®.

As used herein, the term "peptide" refers to a polymer of amino acids linked by amide bonds as is known to those of skill in the art. In a preferred embodiment, the peptide binds to HLA-A2 and is 9 amino acids in length. In another preferred embodiment, the peptide binds to HLA-A2 and is 10 amino acids in length. In another preferred embodiment, the peptide binds to at least one MHC Class II molecule and is 16 amino acids in length. As used herein, the term can refer to a single peptide chain linked by covalent amide bonds. The term can also refer to multiple peptide chains associated by non-covalent interactions such as ionic contacts, hydrogen bonds, Van der Waals contacts and hydrophobic contacts. Those of skill in the art will recognize that the term includes peptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the terms "purified" and "isolated" when used in the context of a peptide that is obtained from a natural source, e.g., cells, refers to a peptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a peptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a peptide that is chemically synthesized refers to a peptide which is substantially free of chemical precursors or other chemicals which are involved in the syntheses of the polypeptide.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

As used herein, the phrase "prophylactic vaccine" refers to a vaccine described herein that is used for the purpose of preventing cancer.

As used herein, the term "prophylactically effective regimen" refers to an effective regimen for dosing, timing, frequency and duration of the administration of one or more therapies for the prevention of brain cancer or a symptom thereof.

As used herein, the term "therapeutic vaccine" refers to a vaccine described herein that is used for the purpose of treating and/or managing brain cancer.

As used herein, the term "therapeutically effective regimen" refers to a regimen for dosing, timing, frequency, and duration of the administration of one or more therapies for the treatment and/or management of brain cancer or a symptom thereof.

As used herein, the terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human toddler. In another embodiment, a subject is a human child. In another embodiment, a subject is a human adult. In another embodiment, a subject is an elderly human.

As used herein, the term "human infant" refers to a newborn to 1 year old human.

As used herein, the term "human toddler" refers to a human that is 1 years to 3 years old.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "brain cancer" refers to a tumor located inside the cranium or in the central spinal canal. Brain cancer refers to both primary tumors (i.e., tumors that originate in the intracranial sphere or the central spinal canal) and secondary tumors (i.e., tumors that invaded the intracranial sphere or the central spinal canal after originating from tumors primarily located in other organs).

As used herein, the terms "therapies" and "therapy" can refer to any protocol(s), method(s), composition(s), formulation(s), and/or agent(s) that can be used in the prevention or treatment of brain cancer or a disease or symptom associated therewith. In certain embodiments, the terms "therapies" and "therapy" refer to biological therapy, supportive therapy, and/or other therapies useful in treatment or prevention of brain cancer or a disease or symptom associated therewith known to one of skill in the art.

As used herein, the term "effective amount" refers to the amount of a therapy that is sufficient to result in the prevention of the development, recurrence, or onset of brain cancer and/or one or more symptoms thereof, to enhance or improve the prophylactic effect(s) of another therapy, reduce the severity, the duration of brain cancer, ameliorate one or more symptoms of brain cancer, prevent the advancement of brain cancer, cause regression of brain cancer, and/or enhance or improve the therapeutic effect(s) of another therapy.

As used herein, the term "in combination" in the context of the administration of a therapy to a subject refers to the use of more than one therapy (e.g., prophylactic and/or therapeutic). The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to brain cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, the terms "manage," "managing," and "management" in the context of the administration of a therapy to a subject refer to the beneficial effects that a subject derives from a therapy (e.g., a prophylactic or therapeutic vaccine) or a combination of therapies, while not resulting in a cure of brain cancer. In certain embodiments, a subject is administered one or more therapies (e.g., one or more prophylactic or therapeutic vaccines) to "manage" brain cancer so as to prevent the progression or worsening of the condition.

As used herein, the terms "prevent," "preventing" and "prevention" in the context of the administration of a therapy to a subject refer to the prevention or inhibition of the recurrence, onset, and/or development of brain cancer or a symptom thereof in a subject resulting from the administration of a therapy (e.g., a prophylactic or therapeutic agent), or a combination of therapies (e.g., a combination of prophylactic or therapeutic agents).

As used herein, the term "concurrently" means sufficiently close in time to produce a combined effect (that is, concurrently may be simultaneously, or it may be two or more events occurring within a time period before or after each other). When administered with other agents, the cancer vaccines provided herein may be administered concurrently with the other active agent. In some embodiments a cancer vaccine provided herein and one or more other agents (e.g., a helper T cell epitope, an adjuvant, and/or an immune response modifier) are administered to a subject concurrently, wherein the administration IL-13Rα2 peptide-based vaccine provided herein and one or more other agents are in the same composition. In other embodiments a cancer vaccine provided herein and one or more other agents (e.g., a helper T cell epitope, an adjuvant, and/or an immune response modifier) are administered to a subject concurrently, wherein the administration of the cancer vaccine provided herein and one or more other agents are not in the same composition. In one embodiment, the agent that is administered concurrently with the cancer vaccine is administered as a separate injection. In certain embodiments, a cancer vaccine provided herein and one or more other agents e.g., a helper T cell epitope, an adjuvant, and/or an immune response modifier) are administered to a subject concurrently, wherein the concurrent administration is separated by at least 1 hour, 2 hours, 3 hours, 4 hours, 5 hours, 10 hours, 12 hours, 1 day, 2 days, 3 days, 4 days, 5 days, 6 days, 1 week, or 2 weeks.

As used herein, the term "brain cancer-associated peptide" refers to a peptide found to be associated with one or more brain cancers and which serves as an HLA-A2 restricted cytotoxic T lymphocyte (CTL) epitope. In some embodiments, a brain cancer-associated peptide is a glioma-associated peptide, i.e., the brain cancer that the peptide is associated with is glioma. In a preferred embodiment, the brain cancer-associated peptide is expressed by glioma cells. Exemplary brain cancer-associated peptides include, without limitation, IL-13Rα2 peptides, EphA2 peptides, and survivin peptides.

As used herein, the term "IL-13Rα2 peptide" refers to a peptide derived from the IL-13Rα2 protein and which serves as an HLA-A2 restricted cytotoxic T lymphocyte (CTL) epitope. In a specific embodiment the IL-13Rα2 protein from which an IL-13Rα2 peptide is derived is the human IL-13Rα2 protein. In another specific embodiment, an IL-13Rα2 peptide comprises any one of SEQ ID NOs:1-4. In some embodiments, an IL-13Rα2 peptide comprises one, two, three, or more amino acid mutations (e.g., additions, substitutions, or deletions) relative to the IL-13Rα2 peptide as it exists in the native (e.g., wild-type) form of the IL-13Rα2 protein.

As used herein, the term "EphA2 peptide" refers to a peptide derived from the EphA2 protein and which serves as an HLA-A2 restricted cytotoxic T lymphocyte (CTL) epitope. In a specific embodiment the EphA2 protein from which an EphA2 peptide is derived is the human EphA2 protein. In another specific embodiment, an EphA2 peptide comprises SEQ ID NO:5. In some embodiments, an EphA2 peptide comprises one, two, three, or more amino acid mutations (e.g., additions, substitutions, or deletions) relative to the EphA2 peptide as it exists in the native (e.g., wild-type) form of the EphA2 protein.

As used herein, the term "survivin peptide" refers to a peptide derived from the survivin protein and which serves as an HLA-A2 restricted cytotoxic T lymphocyte (CTL) epitope. In a specific embodiment the survivin protein from which a survivin peptide is derived is the human survivin protein. In another specific embodiment, a survivin peptide comprises SEQ ID NOs:6-9. In some embodiments, a survivin peptide comprises one, two, three, or more amino acid mutations (e.g., additions, substitutions, or deletions) relative to the survivin peptide as it exists in the native (e.g., wild-type) form of the survivin protein. In some embodiments, the survivin peptide is 9 amino acids in length. In another embodiment, the survivin peptide in 10 amino acids in length.

As used herein, the term "cell-free vaccine" refers to a vaccine comprising synthetic peptides, wherein the peptides are not loaded on a cell (e.g., a dendritic cell) in the vaccine (e.g., the peptides are in solution). In a preferred embodiment, the peptides are emulsified in adjuvant. In another preferred embodiment, the emulsifier is Montanide ISA 51, which is known in certain instances to function as an adjuvant.

As used herein, the term "dendritic cell vaccine" refers to a vaccine comprising a peptide or peptides, wherein the peptide or peptides are loaded on dendritic cells in the vaccine.

BRIEF DESCRIPTION OF THE DRAWINGS

FIGS. 3A-3D depict joint staining of CD133 and IL-13Rα2 cells of the A-172 cancer cell line (FIGS. 3A and 3C), and demonstrates that CD133+ cells of the cell line also express IL-13Rα2 (FIGS. 3B and 3D).

FIGS. 6A-6C demonstrate that the bulk of the cells of the A-172 cancer cell line express EphA2 (FIG. 6B) and IL-13Rα2 (FIG. 6A) at high levels, but only a fraction of these cells express CD133 (FIG. 6C).

FIGS. 7A-7D demonstrate that only a fraction of the cells of the A-172 cancer cell line express CD133.

DETAILED DESCRIPTION

Figure 1C:
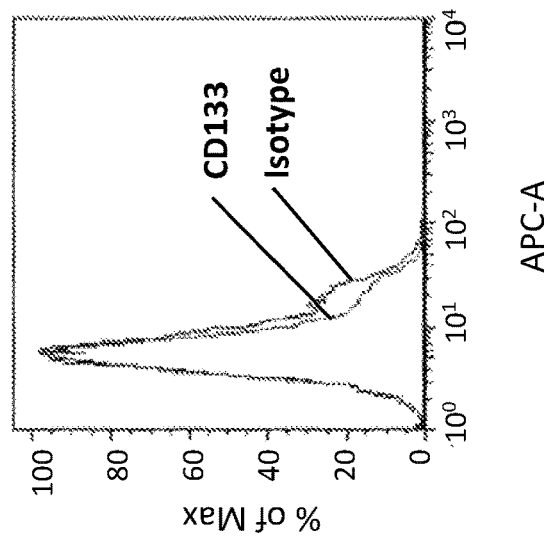
FIGS. 1A-1C demonstrate that the bulk of the cells of the A-172 cancer cell line express EphA2 (FIG. 1A) and IL-13Rα2 (FIG. 1B) at high levels, but only a fraction of these cells express CD133 (FIG. 1C).

Cancer stem cells are attractive targets for cancer immunotherapy. A cancer stem cell(s) of the invention has the ability to re-grow a tumor as demonstrated by its ability to form tumors in immunocompromised mice, and typically to form tumors upon subsequent serial transplantation in immunocompromised mice. Cancer stem cells are also typically slow-growing relative to the remaining bulk of a tumor; that is, cancer stem cells are generally quiescent. In certain embodiments, but not all, the cancer stem cell may represent approximately 0.1 to 10% of a tumor. Moreover, a cancer stem cell(s) may have one or more or all of the following characteristics or properties: (i) can harbor the ability to initiate a tumor and/or to perpetuate tumor growth, (ii) can be generally relatively less mutated than the bulk of a tumor (e.g. due to slower growth and thus fewer DNA replication-dependent errors, improved DNA repair, and/or epigenetic/non-mutagenic changes contributing to their malignancy), (iii) can have many features of a normal stem cell(s) (e.g., similar cell surface antigen and/or intracellular expression profile, self-renewal programs, multi-drug resistance, an immature phenotype, etc., characteristic of normal stem cells) and may be derived from a normal stem cell(s), (iv) can be potentially responsive to its microenvironment (e.g., the cancer stem cells may be capable of being induced to differentiate and/or divide asymmetrically), (v) can be the source of metastases, (vi) can be slow-growing or quiescent, (vii) can be symmetrically-dividing, (viii) can be tumorigenic (e.g. as determined by NOD/SCID implantation experiments), (ix) can be relatively resistant to traditional therapies (i.e. chemoresistant), and (x) can comprise a subpopulation of a tumor (e.g. relative to the tumor bulk).

Provided herein are cancer vaccines that target cancer stem cells, as well as the tumor bulk. Cancer vaccine, as used in herein, is synonymous with cancer stem cell targeted vaccine. The cancer vaccine regimens provided herein comprise tumor associated peptides, helper peptides, emulsifiers, an immune response modifiers administered to patients with cancer in various regimens.

In one aspect, presented herein are cancer vaccines comprising one, two, three, or more cancer-associated peptides. In certain embodiments, the cancer vaccines described herein are administered concurrently with one or more helper T cell epitopes and/or one or more immune response modifiers. In accordance with such embodiments, the one or more helper T cell epitopes and/or one or more immune response modifiers may be administered as part of the vaccine (e.g., in solution with the one, two, three, or more additional cancer-associated peptides) or separate from the vaccine (i.e., the helper T cell epitopes and/or immune response modifiers may be administered as a formulation that is not a part of the formulation containing the peptide(s)). In some embodiments, the cancer vaccines described herein are administered as cell-free vaccines. In other embodiments, the cancer vaccines described herein are administered as dendritic cell vaccines.

In one embodiment, a cancer vaccine comprises an IL-13Rα2 peptide, an EphA2 peptide, and at least one survivin peptide. In a specific embodiment, a cancer vaccine comprises the IL-13Rα2 peptide corresponding to any one of SEQ ID NOs:1-4, the EphA2 peptide corresponding to SEQ ID NO:5, and one or more survivin peptides corresponding to SEQ ID NOs:6-9. In another specific embodiment, a cancer vaccine comprises the IL-13Rα2 peptide corresponding to SEQ ID NO:3, the EphA2 peptide corresponding to SEQ ID NO:5, and the survivin peptide corresponding to SEQ ID NO:7. In another specific embodiment, a cancer vaccine comprises the IL-13Rα2 peptide corresponding to SEQ ID NO:3, the EphA2 peptide corresponding to SEQ ID NO:6, the survivin peptide corresponding to SEQ ID NO:9. In another specific embodiment, the cancer vaccine comprises the IL-13Rα2 peptide corresponding to SEQ ID NO:3, the EphA2 peptide corresponding to SEQ ID NO:6, the survivin peptide corresponding to SEQ ID NO:7, and another survivin peptide corresponding to SEQ ID NO:9. In some embodiments, the cancer vaccine is administered concurrently with one or more helper T cell epitopes. In a specific embodiment, the cancer vaccine is administered concurrently with a helper T cell epitope, wherein the helper T cell epitope is a tetanus toxoid peptide that corresponds with SEQ ID NO:10. In some embodiments, the cancer vaccine is administered concurrently with one or more immune response modifiers. In a specific embodiment, the immune response modifier is GM-CSF. In another specific embodiment, the immune response modifier is imiquimod. In another specific embodiment, the cancer vaccine comprises both GM-CSF and imiquimod. In some embodiments, the cancer vaccine is a cell-free vaccine. In other embodiments, the cancer vaccine is a dendritic cell vaccine.

6.1 Peptides

6.1.1 IL-13Rα2 Peptide

IL-13Rα2 a membrane glycoprotein that binds as a component of a heterodimer to the Th2 cytokine, IL-13, which induces monocytes and macrophages to produce TGFβ (see, e.g., Fichtner-Feigl et al., Nat. Med., 12: 99-106, 2006).

As disclosed herein, IL-13Rα2 is a cancer stem cell antigen (see Example 1; FIGS. 3A-3D and 8B). Accordingly, in certain embodiments, the cancer vaccines provided herein comprise an IL-13Rα2 peptide. Any IL-13Rα2 peptide capable of serving as an HLA-A2 restricted cytotoxic T lymphocyte (CTL) epitope may be used in a vaccine described herein. In some embodiments, the IL-13Rα2 peptide used in a vaccine described herein comprises any one of SEQ ID NOs:1-4. In a specific embodiment, the IL-13Rα2 peptide used in a vaccine described herein comprises SEQ ID NO:3.

In some embodiments, the IL-13Rα2 peptide used in a vaccine described herein comprises a mutated version of SEQ ID NO:1, wherein the mutated version of SEQ ID NO:1 comprises at least 1, at least 2, or at least 3 amino acid substitutions (e.g., conservative substitutions), additions, or deletions.

In some embodiments, the IL-13Rα2 peptide used in a vaccine described herein comprises an amino acid sequence with at least 50%, 60%, 70%, 80%, or 90% identity to SEQ ID NO:1. In other embodiments, the IL-13Rα2 peptide used in a vaccine described herein comprises an amino acid sequence with at least 50% to 60%, 50% to 70%, 60% to 70%, 70% to 80%, 70% to 90%, or 80% to 90% identity to SEQ ID NO:1. In some embodiments, the IL-13Rα2 peptide used in a vaccine described herein comprises an amino acid sequence with at least 50%, 60%, 70%, 80%, or 90% similarity to SEQ ID NO:1. In other embodiments, the IL-13Rα2 peptide used in a vaccine described herein comprises an amino acid sequence with at least 50% to 60%, 50% to 70%, 60% to 70%, 70% to 80%, 70% to 90%, or 80% to 90% similarity to SEQ ID NO:1.

6.1.2 EphA2 Peptide

EphA2 is a tyrosine kinase receptor that is involved in the formation of the notochord via interaction with ephrin A1. (see, e.g., Naruse-Nakajima et al., Mech. Dev., 102: 95-105, 2001).

As disclosed herein, EphA2 is a cancer stem cell antigen (see Example 1; FIGS. 2A-2D and 8A). Accordingly, in certain embodiments, the cancer vaccines provided herein comprise an EphA2 peptide. Any EphA2 peptide capable of serving as an HLA-A2 restricted cytotoxic T lymphocyte (CTL) epitope may be used in a vaccine described herein. In some embodiments, the EphA2 peptide used in a vaccine described herein comprises SEQ ID NO:5. In other embodiments, the EphA2 peptide used in a vaccine described herein is an EphA2 peptide described in U.S. Pat. No. 7,297,337.

In some embodiments, the EphA2 peptide used in a vaccine described herein comprises a mutated version of SEQ ID NO:5, wherein the mutated version of SEQ ID NO:5 comprises at least 1, at least 2, or at least 3 amino acid substitutions (e.g., conservative substitutions), additions, or deletions.

In some embodiments, the EphA2 peptide used in a vaccine described herein comprises an amino acid sequence with at least 50%, 60%, 70%, 80%, or 90% identity to SEQ ID NO:5. In other embodiments, the EphA2 peptide used in a vaccine described herein comprises an amino acid sequence with at least 50% to 60%, 50% to 70%, 60% to 70%, 70% to 80%, 70% to 90%, or 80% to 90% identity to SEQ ID NO:6. In some embodiments, the EphA2 peptide used in a vaccine described herein comprises an amino acid sequence with at least 50%, 60%, 70%, 80%, or 90% similarity to SEQ ID NO:6. In other embodiments, the EphA2 peptide used in a vaccine described herein comprises an amino acid sequence with at least 50% to 60%, 50% to 70%, 60% to 70%, 70% to 80%, 70% to 90%, or 80% to 90% similarity to SEQ ID NO:5.

6.1.3 Survivin Peptide

Survivin is an apoptosis inhibitor protein that is overexpressed in most human cancers, and inhibition of its function results in increased apoptosis (see, e.g., Blanc-Brude et al., Nat. Med., 8: 987-994, 2002).

In some embodiments, the cancer vaccines provided herein comprise a survivin peptide. Any survivin peptide capable of serving as an HLA-A2 restricted cytotoxic T lymphocyte (CTL) epitope may be used in a vaccine described herein. In some embodiments, the survivin peptide used in a vaccine described herein comprises any of the peptides corresponding to SEQ ID NO:6-9. In a specific embodiment, the survivin peptide used in a vaccine described herein comprises SEQ ID NO:7. In another specific embodiment, the survivin peptide used in a vaccine described herein comprises SEQ ID NO:9. In a specific embodiment, the survivin peptide used in a vaccine described herein comprises both peptides corresponding to SEQ ID NO:7 and SEQ ID NO:9. In other embodiments, the survivin peptide used in a vaccine described herein is a survivin peptide described in U.S. Application Publication No. 2009/0041732 or by Ciesielski et al., Cancer Immunol. Immunother., 59:1211-1221, 2010.

In some embodiments, the survivin peptide used in a vaccine described herein comprises a mutated version of SEQ ID NO:6 or SEQ ID NO:8, wherein the mutated version of SEQ ID NO:6 or SEQ ID NO:8 comprises at least 1, at least 2, or at least 3 amino acid substitutions (e.g., conservative substitutions), additions, or deletions.

In some embodiments, the survivin peptide used in a vaccine described herein comprises an amino acid sequence with at least 50%, 60%, 70%, 80%, or 90% identity to SEQ ID NO:6 or SEQ ID NO:8. In other embodiments, the survivin peptide used in a vaccine described herein comprises an amino acid sequence with at least 50% to 60%, 50% to 70%, 60% to 70%, 70% to 80%, 70% to 90%, or 80% to 90% identity to SEQ ID NO:6 or SEQ ID NO:8. In some embodiments, the survivin peptide used in a vaccine described herein comprises an amino acid sequence with at least 50%, 60%, 70%, 80%, or 90% similarity to SEQ ID NO:6 or SEQ ID NO:8. In other embodiments, the survivin peptide used in a vaccine described herein comprises an amino acid sequence with at least 50% to 60%, 50% to 70%, 60% to 70%, 70% to 80%, 70% to 90%, or 80% to 90% similarity to SEQ ID NO:6 or SEQ ID NO:8.

In some embodiments, the survivin peptide used in a vaccine described herein comprises an amino acid sequence with at least 50%, 60%, 70%, 80%, or 90% identity to SEQ ID NO:6 or SEQ ID NO:8. In other embodiments, the survivin peptide used in a vaccine described herein comprises an amino acid sequence with at least 50% to 60%, 50% to 70%, 60% to 70%, 70% to 80%, 70% to 90%, or 80% to 90% identity to SEQ ID NO:6 or SEQ ID NO:8. In some embodiments, the survivin peptide used in a vaccine described herein comprises an amino acid sequence with at least 50%, 60%, 70%, 80%, or 90% similarity to SEQ ID NO:6 or SEQ ID NO:8. In other embodiments, the survivin peptide used in a vaccine described herein comprises an amino acid sequence with at least 50% to 60%, 50% to 70%, 60% to 70%, 70% to 80%, 70% to 90%, or 80% to 90% similarity to SEQ ID NO:6 or SEQ ID NO:8.

6.2 Immunomodulatory Agents and Emulsifiers

In some embodiments, the cancer vaccines provided herein are administered concurrently with an immunomodulatory agent. Immunomodulatory agents are agents capable of modifying the immune response of a subject. In some embodiments, an immune response modifier polarizes the immune response of a subject toward a Th1 response. In other embodiments, an immune response modifier polarizes the immune response of a subject toward a Th2 response. Exemplary immune response modifiers that can be administered concurrently with the cancer stem cell targeted cancer vaccines provided herein include, without limitation, imiquimod (Aldara®; Zyclara®; Beselna®), and GM-CSF (Leukine®, sargramostin, molgramostim, and Leucomax®). In a preferred embodiment, imiquimod and GM-CSF are administered as components of the same cancer stem cell cancer vaccine regimen.

In a preferred embodiment, the immunomodulatory agent is granulocyte-macrophage colony stimulating factor, also known as GM-CSF (Leukine®; sargramostin; molgramostim; Leucomax®). In a preferred embodiment, GM-CSF is administered subcutaneously at a dose of 125 ug per injection. In another preferred embodiment, GM-CSF is administered subcutaneously at a dose of 100 ug per injection. In another preferred embodiment, the GM-CSF is administered in close proximity to the peptide injection. In another preferred embodiment, GM-CSF is administered within 3 centimeters of the peptide injection. In another preferred embodiment, the GM-CSF injection is administered peptide injection is administered within 15 minutes after the peptide injection is administered. In a preferred embodiment, the injections are administered every 3 weeks.

In a preferred embodiment, the immunomodulatory agent is imiquimod (Aldara®, Zyclara®, and Beselna®). In a preferred embodiment, imiquimod is administered topically (on the skin) at the same site as the subcutaneous injections. In another preferred embodiment, imiquimod is administered at a dose of 250 mg in a 5% cream. In another preferred embodiment, the imiquimod is administered topically at the site of the injection of the peptide emulsion and the GM-CSF. In another preferred embodiment, imiquimod is administered topically on the same day as the subcutaneous injections. In another preferred embodiment, imiquimod is administered topically within 15 minutes prior to the subcutaneous injections. In another preferred embodiment, imiquimod is administered topically on the same day as the subcutaneous injections, and 24 hours later. In another preferred embodiment, imiquimod is administered topically on the same day as the subcutaneous injections, and every 24 hours thereafter for 5 days. In a preferred embodiment, the imiquimod is administered topically every 3 weeks.

In some embodiments, the cancer vaccines provided herein are administered concurrently with an adjuvant. In some embodiments, the term "adjuvant" refers to an agent that when administered concurrently with or in the same composition as IL-13Rα2 peptide-based vaccine described herein augments, accelerates, prolongs, enhances and/or boosts the immune response to the cancer vaccine. In some embodiments, the adjuvant generates an immune response to the cancer vaccine and does not produce an allergy or other adverse reaction. Adjuvants can enhance an immune response by several mechanisms including, e.g., lymphocyte recruitment, stimulation of B and/or T cells, stimulation of dendritic cells and stimulation of macrophages.

Specific examples of adjuvants include, but are not limited to, Montanide ISA-51, Montanide ISA 50V, Montanide, ISA 206, Montanide IMS 1312, Vaxlmmune® (CpG7909; Coley Pharmaceuticals), aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents. It should be understood that different formulations of Cancer vaccines may comprise different adjuvants or may comprise the same adjuvant.

6.3 Helper T Cell Epitopes

In some embodiments, the cancer vaccines provided herein are administered concurrently with a helper T cell epitope. Helper T cell epitopes include agents that are capable of inducing a helper T cell response by the immune system. Helper T cells are CD4+ T cells. In some embodiments, helper T cell epitopes are presented by Class II MEW molecules, and may be recognized by the T cell receptor (TCR) of helper T cells (CD4+ T cells), thereby activating the CD4+ T cells, causing them to proliferate, secrete cytokines such as IL2, and activate professional antigen presenting cells. Through a variety of mechanisms, activated helper T cells also stimulate killer T cells (also known as CD8+ T cells), thereby prolonging and increasing the CD8+ T cell response. Exemplary helper T cell epitopes that can be administered concurrently with the cancer vaccines provided herein include, without limitation tetanus toxoid.

6.3.1 Tetanus Toxoid

A well characterized Th epitope (SEQ ID NO:10) from the Tetanus Toxoid (TT) protein, to which the vast majority of the population has been sensitized, is known to act as a helper T cell epitope.

6.4 Production and Purification of Peptides

The peptides described herein can be produced by any method known in the art for the synthesis of peptides, in particular, by chemical synthesis. organic chemistry, biochemistry, and related fields within the skill of the art.

6.4.1.1 Synthetic Production of Peptides

The peptides described herein may be prepared using conventional step-wise solution or solid phase synthesis (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein).

Alternatively, the peptides described herein may be prepared by way of segment condensation, as described, for example, in Liu et al., 1996, Tetrahedron Lett. 37(7):933-936; Baca, et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334. Other methods useful for synthesizing the peptides described herein are described in Nakagawa et al., 1985, J. Am. Chem. Soc. 107:7087-7092.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Hely. Chim. Acta 63:899-915. A method conducted on solid supports is described by Albericio, 1985, Int. J. Peptide Protein Res. 26:92-97, each of which is incorporated by reference herein in its entirety.

6.4.1.2 Purification of Peptides

The peptides described herein and generated using the approaches described in may be purified by any method known in the art for purification of a peptide, for example, by chromatography (e.g., ion exchange, affinity, particularly by affinity for the specific antigen after Protein A, and sizing column chromatography), centrifugation, differential solubility, or by any other standard technique for the purification of proteins. Further, the peptides may be fused to heterologous peptide sequences described herein or otherwise known in the art to facilitate purification. The actual conditions used to purify a particular peptide will depend, in part, on the synthesis strategy (e.g., synthetic production vs. recombinant production) and on factors such as net charge, hydrophobicity, and/or hydrophilicity of the peptide, and will be apparent to those having skill in the art.

6.5 Pharmaceutical Compositions and Routes of Administration

Provided herein are pharmaceutical compositions comprising. In some embodiments, a composition provided herein comprises an interleukin-13 receptor α2 peptide-based brain cancer vaccine. In other embodiments, a composition provided herein comprises a cancer vaccine and a helper T cell epitope, an adjuvant, and/or an immune response modifier. In other embodiments, a composition provided herein comprises an immune response modifier. The pharmaceutical compositions provided herein are suitable for veterinary and/or human administration.

The pharmaceutical compositions provided herein (e.g., a composition comprising a cancer vaccine, a composition comprising a cancer vaccine and a helper T cell epitope, an adjuvant, and/or an immune response modifier, or a composition comprising an immune response modifier) can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In specific embodiments, the compositions provided herein (e.g., a composition comprising a cancer vaccine, a composition comprising a cancer vaccine and a helper T cell epitope, an adjuvant, and/or an immune response modifier, or a composition comprising an immune response modifier) are in the form of a liquid (e.g., an elixir, syrup, solution, emulsion, or suspension). Typical routes of administration of the liquid compositions provided herein may include, without limitation, parenteral, intradermal, intratumoral, intracerebral, and intrathecal. Parenteral administration includes, without limitation, subcutaneous, intranodal, intravenous, intramuscular, intraperitoneal, and intrapleural administration techniques. In a specific embodiment, the compositions are administered parenterally. In a composition for administration by injection, one or more of a surfactant, preservative, wetting agent, dispersing agent, suspending agent, buffer, stabilizer, and isotonic agent may be included. In a specific embodiment, a pump may be used to deliver the vaccines (see, e.g., Sefton, CRC Crit. Ref. Biomed. Eng. 1987, 14, 201; Buchwald et al., Surgery 1980, 88: 507; Saudek et al., N. Engl. J. Med. 1989, 321: 574). In a specific embodiment, the pump may be, but is not limited to, an insulin-like pump.

Materials used in preparing the pharmaceutical compositions provided herein (e.g., a composition comprising a cancer vaccine, a composition comprising a cancer vaccine and a helper T cell epitope, an adjuvant, and/or an immune response modifier, or a composition comprising an immune response modifier) can be non-toxic in the amounts used. It may be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of brain cancer the subject is in need of treatment of, the use of the composition as part of a multi-drug regimen, the particular form of the vaccine being administered, the manner of administration, and the composition employed.

The liquid compositions of the invention, whether they are solutions, suspensions, or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol, or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, or phosphates; and agents for the adjustment of tonicity such as sodium chloride or dextrose. A parenteral composition can be enclosed in an ampoule, a disposable syringe, or a multiple-dose vial made of glass, plastic or other material. An injectable composition is preferably sterile.

The compositions provided herein (e.g., a composition comprising a cancer vaccine, a composition comprising a cancer vaccine and a helper T cell epitope, an adjuvant, and/or an immune response modifier, or a composition comprising an immune response modifier) may comprise a pharmaceutically acceptable carrier or vehicle. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In one embodiment, the compositions provided herein (e.g., a composition comprising a cancer vaccine, a composition comprising a cancer vaccine and a helper T cell epitope, an adjuvant, and/or an immune response modifier, or a composition comprising an immune response modifier) are formulated in accordance with routine procedures as a pharmaceutical composition adapted for parenteral administration to animals, particularly human beings. Generally, the ingredients in the compositions are supplied either separately or mixed together in unit dosage form, for example, as a dry lyophilized powder or water free concentrate in a hermetically sealed container such as an ampoule or sachet indicating the quantity of active agent. Where a composition described herein is administered by injection, an ampoule of sterile water for injection or saline can be provided so that the ingredients can be mixed prior to administration, if necessary.

The compositions provided herein (e.g., a composition comprising a cancer vaccine, a composition comprising a cancer vaccine and a helper T cell epitope, an adjuvant, and/or an immune response modifier, or a composition comprising an immune response modifier) described herein can comprise an additional active agent selected from among those including, but not limited to, an additional prophylactic agent, an additional therapeutic agent, an anti-emetic agent, a hematopoietic colony stimulating factor, an adjuvant therapy, an antibody/antibody fragment-based agent, an anti-depressant and an analgesic agent.

The pharmaceutical compositions provided herein (e.g., a composition comprising a cancer vaccine, a composition comprising a cancer vaccine and a helper T cell epitope, an adjuvant, and/or an immune response modifier, or a composition comprising an immune response modifier) can be prepared using methodology well known in the pharmaceutical art. For example, a composition intended to be administered by injection can be prepared by combining the peptides of a vaccine described herein with water and/or other liquid components so as to form a solution. A surfactant can be added to facilitate the formation of a homogeneous solution or suspension.

The pharmaceutical compositions described herein can be included in a container, pack, or dispenser together with instructions for administration.

6.6 Prophylactic and Therapeutic Uses

In one aspect, provided herein are methods for preventing, treating, and/or managing brain cancer in a subject in need thereof by administering an effective amount of a cancer vaccine described herein.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient a cancer vaccine described herein or a pharmaceutical composition described herein, wherein the patient has been diagnosed with brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient a cancer vaccine described herein or a pharmaceutical composition described herein, wherein the patient has relapsed from brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient a cancer vaccine described herein or a pharmaceutical composition described herein, wherein the patient has failed or is failing brain cancer therapy that does not comprise a vaccine described herein.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient a cancer vaccine described herein or a pharmaceutical composition described herein, wherein the patient is in remission from brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient a cancer vaccine described herein or a pharmaceutical composition described herein, wherein the patient is refractory to brain cancer therapy that does not comprise a vaccine described herein. In one embodiment of this aspect, the patient has received or is receiving brain cancer therapy that does not comprise a vaccine described herein. In another embodiment of this aspect, the patient has not previously received a brain cancer therapy that does not comprise a vaccine described herein for the prevention, treatment, and/or management of the brain cancer.

In another aspect, provided herein is a method of preventing, treating, and/or managing brain cancer in a patient (e.g., a human patient), the method comprising administering to the patient a prophylactically effective regimen or a therapeutically effective regimen, the regimen comprising administering to the patient a cancer vaccine described herein or a pharmaceutical composition described herein, wherein the patient has received another brain cancer therapy. In some embodiments, the prior brain cancer therapy is, for example, chemotherapy, radiation therapy, surgical therapy, small molecule therapy, biologic therapy, antibody therapy, hormone therapy, immunotherapy, anti-angiogenic therapy or any combination thereof. In some embodiments, the prior therapy has failed in the patient. In some embodiments, the therapeutically effective regimen comprising administration of a cancer vaccine described herein is administered to the patient immediately after the patient has undergone the prior therapy. For instance, in certain embodiments, the outcome of the prior therapy may be unknown before the patient is administered the cancer vaccine. In one embodiment, the prior chemotherapy is temolozimide. In embodiment, the prior therapy is radiation therapy. In another embodiment, the prior therapy is a combination of temozolomide and radiation therapy. In a preferred embodiment, the combination of temozolomide and radiation are administered using the Stupp regimen. In another embodiment, the prior therapy is surgery. In some embodiments, the patient undergoes surgery before the initiation of combination therapy. In some embodiments, the patient undergoes surgery before treatment with temozolomide. In some embodiments, the patient undergoes surgery before the initiation of radiation therapy. In each of these embodiments that describe the use of combination therapy, the cancer vaccine may be administered before, during, or after the treatment of the patient with the therapy that is being combined.

In some embodiments, the cancer vaccines described herein are administered as monotherapy for the prevention, treatment, and/or management of brain cancer. In other embodiments, provided herein are methods comprising administering to a subject in need thereof a cancer vaccine described herein and one or more agents other than the cancer vaccine described herein that are currently being used, have been used, are known to be useful, or may be useful in the prevention, treatment, and/or management of brain cancer or one or more symptoms thereof. The agents of the combination therapies can be administered sequentially or concurrently. In certain embodiments, the combination therapies improve the prophylactic or therapeutic effect of a cancer vaccine described herein functioning together with the cancer vaccine described herein to have an additive or synergistic effect. In some embodiments, the combination therapies are administered prior to, during, or after the administration of the compositions described herein.

In another aspect, provided herein are methods for inducing an immune response in a subject with brain cancer comprising administering an effective amount of a cancer vaccine described herein. In some embodiments, the immune response induced in a subject by a cancer vaccine described herein or a composition described herein is effective to prevent, treat, and/or manage brain cancer in the subject. In some embodiments, the immune response induced in a subject by a cancer vaccine described herein or a composition described herein is effective to reduce symptoms of brain cancer in the subject.

The medical practitioner can diagnose the patient using any of the conventional brain cancer screening methods including, but not limited to neurological examination; imaging methods (e.g., computed tomography (CT), magnetic resonance imaging (MRI), ultrasound, X-ray imaging, and positron emission tomography (PET) scans); and biopsy (e.g., sterotactic biopsy).

6.6.1 Dosage and Frequency of Administration

The amount of a composition described herein (e.g., a composition comprising a cancer vaccine, a composition comprising a cancer vaccine and a helper T cell epitope, an adjuvant, and/or an immune response modifier, or a composition comprising an immune response modifier) which will be effective in the treatment, prevention, and or management of brain cancer may depend on the status of the brain cancer, the patient to whom the composition(s) is to be administered, the route of administration, and/or the type of brain cancer. Such doses can be determined by standard clinical techniques and may be decided according to the judgment of the practitioner.

For example, effective doses may vary depending upon means of administration, target site, physiological state of the patient (including age, body weight, and health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

In certain embodiments, the cancer vaccine is a cell-free vaccine, wherein the cell-free vaccine comprises an IL-13Rα2 peptide and one, two, three, or more additional brain cancer-associated peptides. In some embodiments, exemplary cell-free Cancer vaccines comprise about 25, 50, 75, 100, 125, 150, 175, 200, 225, 250, 275, 300, 325, 350, 375, 400, 425, 450, 475, 500, 550, 600, 650, 700, 750, or 800 µg of each brain cancer-associated peptide per dose. In other embodiments, exemplary cell-free Cancer vaccines comprise about 25 to 50, 25 to 75, 25 to 100, 50 to 100, 50 to 150, 50 to 200, 100 to 150, 100 to 200, 100 to 250, 100 to 300, 150 to 200, 150 to 250, 150 to 300, 200 to 250, 250 to 300, 250 to 350, 250 to 400, 300 to 350, 300 to 400, 300 to 450, 300 to 500, 350 to 400, 350 to 450, 400 to 500, 400 to 600, 500 to 600, 500 to 700, 600 to 700, 600 to 800, or 700 to 800 µg of each brain cancer-associated peptide per dose. In other embodiments, exemplary cell-free Cancer vaccines comprise about 5 µg to 100 mg, 15 µg to 50 mg, 15 µg to 25 mg, 15 µg to 10 mg, 15 µg to 5 mg, 15 µg to 1 mg, 15 µg to 100 µg, 15 µg to 75 µg, 5 µg to 50 µg, 10 µg to 50 µg, 15 µg to 45 µg, 20 µg to 40 µg, or 25 to 35 µg of each brain cancer-associated peptide per kilogram of the patient.

In certain embodiments, the cell-free Cancer vaccines are administered concurrently with a helper T cell epitope. In some embodiments, exemplary cell-free Cancer vaccines are administered concurrently with about 25, 50, 75, 100, 125, 150, 175, 200, 225, 250, 275, 300, 325, 350, 375, 400, 425, 450, 475, 500, 550, or 600 µg of a helper T cell epitope. In other embodiments, exemplary cell-free Cancer vaccines are administered concurrently with about 25 to 50, 25 to 75, 25 to 100, 50 to 100, 50 to 150, 50 to 200, 100 to 150, 100 to 200, 100 to 250, 100 to 300, 150 to 200, 150 to 250, 150 to 300, 200 to 250, 250 to 300, 250 to 350, 250 to 400, 300 to 350, 300 to 400, 300 to 450, 300 to 500, 350 to 400, 350 to 450, 400 to 500, 400 to 600, or 500 to 600 µg of a helper T cell epitope.

In certain embodiments, the cell-free cancer vaccines are administered concurrently with an immune response modifier. In some embodiments, exemplary cell-free cancer vaccines are administered concurrently with about 100, 200, 300, 400, 500, 600, 700, 800, 900, 1000, 1100, 1200, 1300, 1400, 1500, 1600, 1700, or 1800 µg of an immune response modifier. In other embodiments, exemplary cell-free cancer vaccines are administered concurrently with about 100 to 300, 200 to 400, 400 to 800, 600 to 800, 800 to 1000, 800 to 1200, 1000 to 1200, 1000 to 1400, 1200 to 1400, 1200 to 1600, 1400 to 1600, 1400 to 1800, or 1600 to 1800 µg of an immune response modifier. In other embodiments, exemplary cell-free cancer vaccines are administered concurrently with about 1, 5, 10, 15, 20, 25, 30, 35, 40, 45, 50, 55, or 60 µg of an immune response modifier per kilogram of the patient. In other embodiments, exemplary cell-free cancer vaccines are administered concurrently with about 1 to 5, 1 to 10, 5 to 10, 5 to 15, 10 to 15, 10 to 20, 15 to 20, 15 to 25, 15 to 30, 20 to 25, 20 to 30, 20 to 35, 25 to 30, 25 to 35, 25 to 40, 30 to 35, 30 to 40, 35 to 40, 35 to 45, 40 to 45, 40 to 50, 45 to 50, 50 to 55, or 50 to 60 µg of an immune response modifier per kilogram of the patient.

In certain embodiments, the cell-free cancer vaccines are administered concurrently with an adjuvant. In some embodiments, a composition comprising a cell-free IL-13Rα2 peptide-based vaccine is mixed 0.5 to 1, 1 to 0.5, 1 to 1, 1 to 2, 1 to 3, 2 to 1, or 3 to 1 with an adjuvant.

In certain embodiments, the cancer vaccine is a dendritic cell-based vaccine, wherein the dendritic cell-based vaccine comprises dendritic cells loaded with an IL-13Rα2 peptide and dendritic cells loaded with one, two, three, or more additional brain cancer-associated peptides. In some embodiments, exemplary dendritic cell-based cancer vaccines comprise about $10^3$, $5\times10^3$, $10^4$, $5\times10^4$, $10^5$, $5\times10^5$, $10^6$, $5\times10^6$, $10^7$, $3\times10^7$, $5\times10^7$, $7\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ dendritic cells loaded with brain cancer-associated peptide(s) per dose. In other embodiments, exemplary dendritic cell-based cancer vaccines comprise about $10^3$ to $10^4$, $10^3$ to $10^5$, $10^4$ to $10^5$, $10^4$ to $10^6$, $10^5$ to $10^6$, $10^5$ to $10^7$, $10^6$ to $10^7$, $10^6$ to $10^8$, $10^7$ to $10^8$, $10^7$ to $10^9$, $10^8$ to $10^9$, $10^9$ to $10^{10}$, $10^{10}$ to $10^{11}$, or $10^{11}$ to $10^{12}$ dendritic cells loaded with brain cancer-associated peptide(s) per dose.

In certain embodiments, the dendritic cell-based cancer vaccines are administered concurrently with a helper T cell epitope. In some embodiments, exemplary dendritic cell-based cancer vaccines are administered concurrently with about 25, 50, 75, 100, 125, 150, 175, 200, 225, 250, 275, 300, 325, 350, 375, 400, 425, 450, 475, 500, 550, or 600 μg of a helper T cell epitope. In other embodiments, exemplary dendritic cell-based cancer vaccines are administered concurrently with about 25 to 50, 25 to 75, 25 to 100, 50 to 100, 50 to 150, 50 to 200, 100 to 150, 100 to 200, 100 to 250, 100 to 300, 150 to 200, 150 to 250, 150 to 300, 200 to 250, 250 to 300, 250 to 350, 250 to 400, 300 to 350, 300 to 400, 300 to 450, 300 to 500, 350 to 400, 350 to 450, 400 to 500, 400 to 600, or 500 to 600 μg of a helper T cell epitope.

In a preferred embodiment, the helper T cell epitope is the tetanus toxoid peptide (SEQ ID No: 10) and is administered at a dose of In certain embodiments, the dendritic cell-based cancer vaccines are administered concurrently with an immune response modifier. In some embodiments, exemplary dendritic cell-based cancer vaccines are administered concurrently with about 100, 200, 300, 400, 500, 600, 700, 800, 900, 1000, 1100, 1200, 1300, 1400, 1500, 1600, 1700, or 1800 μg of an immune response modifier. In other embodiments, exemplary dendritic cell-based cancer vaccines are administered concurrently with about 100 to 300, 200 to 400, 400 to 800, 600 to 800, 800 to 1000, 800 to 1200, 1000 to 1200, 1000 to 1400, 1200 to 1400, 1200 to 1600, 1400 to 1600, 1400 to 1800, or 1600 to 1800 μg of an immune response modifier. In other embodiments, exemplary dendritic cell-based cancer vaccines are administered concurrently with about 1, 5, 10, 15, 20, 25, 30, 35, 40, 45, 50, 55, or 60 μg of an immune response modifier per kilogram of the patient. In other embodiments, exemplary dendritic cell-based cancer vaccines are administered concurrently with about 1 to 5, 1 to 10, 5 to 10, 5 to 15, 10 to 15, 10 to 20, 15 to 20, 15 to 25, 15 to 30, 20 to 25, 20 to 30, 20 to 35, 25 to 30, 25 to 35, 25 to 40, 30 to 35, 30 to 40, 35 to 40, 35 to 45, 40 to 45, 40 to 50, 45 to 50, 50 to 55, or 50 to 60 μg of an immune response modifier per kilogram of the patient.

In certain embodiments, the dendritic cell-based cancer vaccines are administered concurrently with an adjuvant. In some embodiments, a composition comprising a dendritic cell-based IL-13Rα2 peptide-based vaccine is mixed 0.5 to 1, 1 to 0.5, 1 to 1, 1 to 2, 1 to 3, 2 to 1, or 3 to 1 with an adjuvant.

In certain embodiments, a composition described herein (e.g., a composition comprising a cancer vaccine, a composition comprising a cancer vaccine and a helper T cell epitope, an adjuvant, and/or an immune response modifier, or a composition comprising an immune response modifier) is administered to a subject once as a single dose. In some embodiments, a composition described herein (e.g., a composition comprising a cancer vaccine, a composition comprising a cancer vaccine and a helper T cell epitope, an adjuvant, and/or an immune response modifier, or a composition comprising an immune response modifier) is administered in multiple doses (e.g., 1, 2, 3, 4, 5, 6, 7, 8, 9, 10, or more than 10 doses), wherein the doses may be separated by at least 1 day, 2 days, 3 days, 4, days 5 days, 6 days, 7 days, 8 days, 9 days, 10 days, 15 days, or 30 days. In specific embodiments, the cancer vaccine is administered intranodally or subcutaneously and the immune response modifier is administered intramuscularly.

In some embodiments, when a composition described herein comprises a cell-free cancer stem cell targeted cancer vaccine, the composition may be administered over the course of 21 weeks, with administrations occurring on weeks 0, 3, 6, 9, 12, 15, 18 and 21. In certain embodiments, the composition comprising a cell-free cancer stem cell targeted cancer vaccine is administered concurrently with a helper T cell epitope, an adjuvant, and/or an immune response modifier. In a specific embodiment, a composition described herein comprising a cell-free cancer stem cell targeted cancer vaccine is administered over the course of 21 weeks, with administrations occurring on weeks 0, 3, 6, 9, 12, 15, 18 and 21, and the composition is administered concurrently with an immune response modifier, wherein the immune response modifier is administered on the day of each administration of the cell-free cancer stem cell targeted cancer vaccine and on day 4 after each administration of the cell-free cancer stem cell targeted cancer vaccine. In another specific embodiment, a composition described herein comprising a cell-free cancer stem cell targeted cancer vaccine is administered over the course of 21 weeks, with administrations occurring on weeks 0, 3, 6, 9, 12, 15, 18 and 21, and the composition is administered concurrently with an immune response modifier, wherein the immunomodulatory agent is administered on the day of each administration of the cell-free cancer stem cell targeted cancer vaccine. In specific embodiments, the cell-free cancer stem cell targeted cancer vaccine is administered subcutaneously and the immunomodulatory agent is administered subcutaneously. In other specific embodiments, the cell-free cancer stem cell targeted cancer vaccine is administered subcutaneously and one immunomodulatory agent is administered subcutaneously, and another immunomodulatory agent is administered topically.

In some embodiments, when a composition described herein comprises a dendritic cell-based cancer stem cell targeted cancer vaccine, the composition may be administered over the course of 6 weeks, with administrations occurring on weeks 0, 2, 4, and 6. In certain embodiments, the composition comprising a cell-free cancer stem cell targeted cancer vaccine is administered concurrently with a helper T cell epitope, an adjuvant, and/or an immune response modifier. In a specific embodiment, a composition described herein comprising a dendritic cell-based cancer stem cell targeted cancer vaccine is administered over the course of 6 weeks, with administrations occurring on weeks 0, 2, 4, and 6, and the composition is administered concurrently with an immune response modifier, wherein the immune response modifier is administered twice per week beginning on the first day of administration of the dendritic cell-based cancer stem cell targeted cancer vaccine. In specific embodiments, the dendritic cell-based cancer stem cell targeted cancer vaccine is administered intranodally and the immune response modifier is administered intramuscularly.

In some embodiments, when a composition described herein comprises a dendritic cell-based cancer stem cell targeted cancer vaccine, the composition may be administered over the course of 26 weeks, with administrations occurring on weeks 0, 2, 4, 6, 10, 14, 18, 22, and 26. In certain embodiments, the composition comprising a cell-free IL-13Rα2 peptide-based vaccine is administered concurrently with a helper T cell epitope, an adjuvant, and/or an immune response modifier. In a specific embodiment, a composition described herein comprising a dendritic cell-based cancer stem cell targeted cancer vaccine is administered over the course of 26 weeks, with administrations occurring on weeks 0, 2, 4, 6, 10, 14, 18, 22, and 26, and the composition is administered concurrently with an immune response modifier, wherein the immune response modifier is administered twice per week beginning on the first day of administration of the dendritic cell-based cancer stem cell targeted cancer vaccine. In specific embodiments, the dendritic cell-based cancer stem cell targeted cancer vaccine is administered intranodally and the immune response modifier is administered intramuscularly.

6.6.2 Brain Cancers

The cancer vaccine described herein can be used in the prevention, treatment, and/or management of brain cancer. Any type of brain cancer can be treated with the cancer vaccines described herein in accordance with the methods described herein. Exemplary brain cancers include, but are not limited to, gliomas (including astrocytoma (e.g., pilocytic astrocytoma, diffuse astrocytoma, and anaplastic astrocytoma), glioblastoma, oligodendroglioma, brain stem glioma, non-brain stem glioma, ependymoma, and mixed tumors comprising more than one glial cell types), acoustic schwannoma, cranialpharyngioma, meningioma, medulloblastoma, primary central nervous system lymphoma, and tumors of the pineal (e.g., pineal astrocytic tumors and pineal parenchymal tumors) and pituitary glands. Gliomas additionally include recurrent malignant gliomas, high-risk WHO Grade II Astrocytomas, Oligo Astrocytomas, recurrent WHO Grade II Gliomas, newly-diagnosed malignant or intrinsic brain stem gliomas, incompletely resected non-brainstem gliomas, and recurrent unresectable low-grade gliomas. Additional types of brain cancer that can be treated with the cancer vaccines described herein in accordance with the methods described herein include adult low-grade infiltrative supratentorial astrocytoma/oligodendroglioma, adult low-grade infiltrative supratentorial astrocytoma, adult low-grade infiltrative supratentorial oligodendroglioma, adult low-grade infiltrative supratentorial astrocytoma/oligodendroglioma (excluding pilocytic astrocytoma), adult low-grade infiltrative supratentorial astrocytoma (excluding pilocytic astrocytoma), adult low-grade infiltrative supratentorial oligodendroglioma (excluding pilocytic astrocytoma), adult intracranial ependymoma, adult intracranial ependymoma (excluding subependymoma and myxopapillary), adult intracranial anaplastic ependymoma, anaplastic glioma, anaplastic glioblastoma, pilocytic astrocytoma, subependymoma, myxopapillary, 1 to 3 limited metastatic lesions (intraparenchymal), greater than 3 metastatic lesions (intraparenchymal), leptomeningeal metastases (neoplastic meningitis), primary CNS lymphoma, metastatic spine tumors, or meningiomas.

In one embodiment, the brain cancer treated with the cancer vaccines described herein in accordance with the methods described herein is a glioma. In a specific embodiment, the brain cancer treated with the cancer vaccines described herein in accordance with the methods described herein is recurrent malignant glioma. In another specific embodiment, the brain cancer treated with the cancer vaccines described herein in accordance with the methods described herein is recurrent WHO Grade II Glioma. In another specific embodiment, the brain cancer treated with the cancer vaccines described herein in accordance with the methods described herein is newly-diagnosed malignant or intrinsic brain stem glioma. In another specific embodiment, the brain cancer treated with the cancer vaccines described herein in accordance with the methods described herein is incompletely resected non-brainstem glioma. In another specific embodiment, the brain cancer treated with the cancer vaccines described herein in accordance with the methods described herein is recurrent unresectable low-grade glioma. In one embodiment, the patient is an adult with recurrent malignant glioma, recurrent glioblastoma, anaplastic astrocytoma, anaplastic oligodendroglioma, or anaplastic mixed oligoastrocytoma. In another specific embodiment, the patient is an adult with newly diagnosed high-risk low grade glioma. In another specific embodiment, the patient is an adult with newly diagnosed high-risk low grade astrocytoma. In another specific embodiment, the patient is an adult with newly diagnosed high-risk low grade oligoastrocytoma. In another specific embodiment, the patient is an adult with recurrent high-risk low grade astrocytoma. In another specific embodiment, the patient is an adult with recurrent high-risk low grade oligoastrocytoma. In another specific embodiment, the patient is an adult with recurrent high-risk low grade oligodendroglioma. In another specific embodiment, the patient is a child with newly diagnosed malignant glioma. In another specific embodiment, the patient is a child with intrinsic brain stem glioma. In another specific embodiment, the patient is a child with incompletely resected non-brainstem high-grade glioma. In another specific embodiment, the patient is a child with recurrent unresectable low-grade glioma. In another specific embodiment, the patient is a child with newly diagnosed diffuse intrinsic pontine glioma. In another specific embodiment, the patient is a child with any high-grade glioma involving the brainstem and treated with RT or without chemotherapy during RT. In another specific embodiment, the patient is a child with newly diagnosed non-brainstem high-grad glioma treated with RT with chemotherapy. In another specific embodiment, the patient is a child with newly diagnosed non-brainstem high-grad glioma treated with RT without chemotherapy. In another specific embodiment, the patient is a child with recurrent non-brainstem high-grade glioma that has recurred after treatment.

In another embodiment, the brain cancer treated with the cancer vaccines described herein in accordance with the methods described herein is an astrocytoma. In a specific embodiment, the brain cancer treated with the cancer vaccines described herein in accordance with the methods described herein is high-risk WHO Grade II Astrocytoma. In another specific embodiment, the brain cancer treated with the cancer vaccines described herein in accordance with the methods described herein is Oligo Astrocytoma.

6.6.3 Patient Populations

In certain a cancer vaccine or composition described herein may be administered to a naïve subject, i.e., a subject that does not have brain cancer. In one embodiment, a cancer vaccine or composition described herein is administered to a naïve subject that is at risk of acquiring brain cancer.

In certain embodiments, a cancer vaccine or composition described herein is administered to a patient who has been diagnosed with brain cancer. In some embodiments, a cancer vaccine or composition described herein is administered to a patient with brain cancer before symptoms manifest or symptoms become severe. In a preferred embodiment, the brain cancer is glioma.

In certain embodiments, a cancer vaccine or composition described herein is administered to a patient who is in need of treatment, prevention, and/or management of brain cancer. Such subjects may or may not have been previously treated for cancer or may be in remission, relapsed, or may have failed treatment. Such patients may also have abnormal cytogenetics. The cancer stem cell targeted cancer vaccines and compositions described herein may be used as any line of brain cancer therapy, e.g., a first line, second line, or third line of brain cancer therapy. In a specific embodiment, the subject to receive or receiving a vaccine or pharmaceutical composition described herein is receiving or has received other brain cancer therapies. In an alternative embodiment, the subject to receive or receiving a vaccine or pharmaceutical composition described herein has not received or is not receiving other brain cancer therapies.

In a specific embodiment, the subject has been diagnosed with brain cancer using techniques known to one of skill in the art including, but not limited to, neurological examination; imaging methods (e.g., computed tomography (CT), magnetic resonance imaging (MRI), ultrasound, X-ray imaging, fluid-attenuated inversion-recovery (FLAIR) sequences, T2 weighted imaging, and positron emission tomography (PET) scans); and biopsy (e.g., sterotactic biopsy). Tumor response to therapy may be evaluated by McDonald criteria or Response assessment in neuro-oncology (RANO) criteria. Tumor size or response to treatment can be evaluated by various magnetic resonance imaging techniques including diffusion-weighted imaging, perfusion-weighted imaging, dynamic contrast-enhanced T1 permeability imaging, dynamic susceptibility contrast, diffusion-tensor imaging, and magnetic resonance spectroscopy, anatomic MRI T2-weighted images, fluid attenuated inversion recovery (FLAIR) T2-weighted images, and gadolinium-enhanced T1-weighted images. These imagining techniques can be used to assess tumor cellularity, white matter invasion, metabolic derangement including hypoxia and necrosis, neovascular capillary blood volume, or permeability. Positron emission tomograph (PET) technology can also be used to image tumor response, such as 18F-fluoromisonidazole PET and 3'-deoxy-3'-18F-fluorothymidine PET.

In one embodiment, a cancer vaccine or composition described herein is administered to a subject that is undergoing or has undergone radiation therapy to treat a brain cancer tumor. In a specific embodiment, a cancer vaccine or composition described herein is administered to a subject concurrently or following radiation therapy to treat a brain cancer tumor. In another embodiment, a cancer vaccine or composition described herein is administered to a subject before radiation therapy to treat a brain cancer tumor and, in some embodiments, during and/or after the radiation therapy. In some preferred embodiments, the radiation therapy is fractionated external beam radiotherapy, limited-field fractionated external beam radiotherapy, whole brain radiotherapy, stereotactic radiosurgery, or craniospinal radiotherapy In one embodiment, a cancer vaccine or composition described herein is administered to a subject that is undergoing or has undergone chemotherapy to treat a brain cancer tumor. In a specific embodiment, a cancer vaccine or composition described herein is administered to a subject concurrently or following chemotherapy to treat a brain cancer tumor. In another embodiment, a cancer vaccine or composition described herein is administered to a subject before chemotherapy to treat a brain cancer tumor and, in some embodiments, during and/or after the chemotherapy. In some preferred embodiments, the chemotherapy is temozolomide (Temodar®), nitrosurea, platinum-based regimens, etoposide, cisplatin, bevacizumab (Avastin®), irinotecan, cyclophosphamide, BCNU (carmustine), capecitabine, high-dose methotrexate, topotecan, high-dose ARA-C, hydroxyurea, α-interferon, somatostatin analogue, intra-CSF chemotherapy (liposomal cytarabine, methotrexate, cytarabine, thiotepa, or rituximab (Rituxan®)).

In one embodiment, a cancer vaccine or composition described herein is administered to a subject that has failed, is undergoing or has undergone more than one therapeutic strategy, including chemotherapy, radiation therapy, or surgery to treat a brain cancer tumor. In a preferred embodiment, the brain cancer is glioma. For example, a patient may be failed, be undergoing, or have undergone both chemotherapy and surgery. Alternatively, a patient may have undergone or be undergoing both radiation and surgery. Moreover, a patient may have undergone or be undergoing chemotherapy and radiation. In some preferred embodiments, the combined therapies that the patient failed, is undergoing, or has undergone are resection and temozolomide (Temodar®) (150-200 mg/m$^2$) 5/28 schedule, resection and BCNU wafer (Gliader®), bevacizumab (Avastin®) and chemotherapy, combination PCV (CCNU (lomustine) and procarbazine and vincristine), high-dose methotrexate and vincristine, procarbazine, cytaribine, or rituximab, high-dose chemotherapy with stem cell rescue, or rituximab (Rituxan®) and temozolomide (Temodar®).

In one embodiment, a cancer vaccine or composition described herein is administered to a subject that is undergoing or has undergone surgery to remove a brain cancer tumor. In a specific embodiment, a cancer vaccine or composition described herein is administered to a subject concurrently or following surgery to remove a brain cancer tumor. In another embodiment, a cancer vaccine or composition described herein is administered to a subject before surgery to remove a brain cancer tumor and, in some embodiments, during and/or after surgery.

In certain embodiments, a cancer vaccine or composition described herein is administered to a subject as an alternative to another therapy, e.g., chemotherapy, radiation therapy, hormonal therapy, surgery, small molecule therapy, anti-angiogenic therapy, and/or biological therapy including immunotherapy where the therapy has proven or may prove too toxic, i.e., results in unacceptable or unbearable side effects for the subject.

In a specific embodiment, a cancer vaccine or composition described herein is administered to subjects that will have, are undergoing, or have had radiation therapy. Among these subjects are those that have received chemotherapy, hormonal therapy, small molecule therapy, anti-angiogenic therapy, and/or biological therapy, including immunotherapy as well as those who have undergone surgery.

In another embodiment, a cancer vaccine or composition described herein is administered to subjects that will have, are undergoing, or have had hormonal therapy and/or biological therapy, including immunotherapy. Among these subjects are those that have received chemotherapy, small molecule therapy, anti-angiogenic therapy, and/or radiation therapy as well as those who have undergone surgery.

In certain embodiments, a cancer vaccine or composition described herein is administered to a subject refractory to one or more therapies. In one embodiment, that a cancer is refractory to a therapy means that at least some significant portion of the cancer cells are not killed or their cell division is not arrested. The determination of whether the cancer cells are refractory can be made either in vivo or in vitro by any method known in the art for assaying the effectiveness of a therapy on cancer cells, using the art-accepted meanings of "refractory" in such a context. In various embodiments, a cancer is refractory where the amount of cancer cells has not been significantly reduced, or has increased.

In some embodiments, a cancer vaccine or composition described herein is administered to a subject that is in remission from brain cancer. In a specific embodiment, the subject has no detectable brain cancer, i.e., no brain cancer is detectable using a conventional method described herein (e.g., MRI) or known to one of skill in the art.

In one embodiment, a cancer vaccine or composition described herein is administered to a subject diagnosed with glioma. In a specific embodiment, a cancer vaccine or composition described herein is administered to a subject diagnosed with astrocytoma (e.g., pilocytic astrocytoma, diffuse astrocytoma, and anaplastic astrocytoma). In another specific embodiment, a cancer vaccine or composition described herein is administered to a subject diagnosed with glioblastoma. In another specific embodiment, a cancer vaccine or composition described herein is administered to a subject diagnosed with oligodendroglioma. In another specific embodiment, a cancer vaccine or composition described herein is administered to a subject diagnosed with brain stem glioma. In another specific embodiment, a cancer vaccine or composition described herein is administered to a subject diagnosed with ependymoma. In another specific embodiment, a cancer vaccine or composition described herein is administered to a subject diagnosed with a mixed tumor comprising more than one glial cell types.

In a specific embodiment, a cancer vaccine or composition described herein is administered to a subject diagnosed with recurrent malignant glioma. In another specific embodiment, a cancer vaccine or composition described herein is administered to a subject diagnosed with high-risk WHO Grade II Astrocytomas. In another specific embodiment, a cancer vaccine or composition described herein is administered to a subject diagnosed with Oligo Astrocytoma. In another specific embodiment, a cancer vaccine or composition described herein is administered to a subject diagnosed with recurrent WHO Grade II Glioma. In another specific embodiment, a cancer vaccine or composition described herein is administered to a subject diagnosed with newly-diagnosed malignant or intrinsic brain stem glioma. In another specific embodiment, a cancer vaccine or composition described herein is administered to a subject diagnosed with incompletely resected non-brainstem glioma. In another specific embodiment, a cancer vaccine or composition described herein is administered to a subject diagnosed with recurrent unresectable low-grade glioma.

In a specific embodiment, a cancer vaccine or composition described herein is administered to a subject diagnosed with acoustic schwannoma. In another specific embodiment, a cancer vaccine or composition described herein is administered to a subject diagnosed with cranial pharyngioma. In another specific embodiment, a cancer vaccine or composition described herein is administered to a subject diagnosed with meningioma. In another specific embodiment, a cancer vaccine or composition described herein is administered to a subject diagnosed with medulloblastoma. In another specific embodiment, a cancer vaccine or composition described herein is administered to a subject diagnosed with primary central nervous system lymphoma. In another specific embodiment, a cancer vaccine or composition described herein is administered to a subject diagnosed with a tumor of the pineal gland (e.g., a pineal astrocytic tumor or a pineal parenchymal tumor). In another specific embodiment, a cancer vaccine or composition described herein is administered to a subject diagnosed with a tumor of the pituitary gland.

In certain embodiments, a subject to be administered a cancer vaccine or composition described herein is a human adult. In certain embodiments, a subject to be administered a cancer vaccine or composition described herein is an elderly human subject. In certain embodiments, a subject to be administered a cancer vaccine or composition described herein is a human child. In certain embodiments, a subject to be administered a cancer vaccine or composition described herein is a human infant. In certain embodiments, a subject to be administered a cancer vaccine or composition described herein is a human toddler.

In certain embodiments, a subject to be administered a cancer vaccine or composition described herein is HLA-A2 positive as determined by, e.g., flow cytometry.

In certain embodiments, a subject to be administered a cancer vaccine or composition described herein has a Karnofsky performance status (KPS) of >60. The KPS is used as a stratification and selection variable in randomized trials of chemotherapeutic agents and has a range of 0-100. Patients with a score>60 are unable to work, are able to live at home, and can care for most of their personal needs with varying degrees of required assistance. Patients with a score>70 carry on normal activity with effort and show some signs and symptoms of the disease. Patients with a score>80 are able to carry on normal activity and only show minor signs or symptoms of the disease. Patients with a score>90 are normal, have no health complaints, and show no signs or symptoms of the disease.

In certain embodiments, a subject to be administered a cancer vaccine or composition described herein has a white blood count of about $1000/mm^3$, $1500/mm^3$, $2000/mm^3$, $2500/mm^3$, $3000/mm^3$, or $3500/mm^3$ or about $1000/mm^3$ to $1500/mm^3$, $1000/mm^3$ to $2000/mm^3$, $1500/mm^3$ to $2500/mm^3$, $1500/mm^3$ to $3000/mm^3$, $2000/mm^3$ to $3500/mm^3$, or $2500/mm^3$ to $3500/mm^3$. In a specific embodiment, a subject to be administered a cancer vaccine or composition described herein has a white blood count greater than or equal to $2500/mm^3$.

In certain embodiments, a subject to be administered a cancer vaccine or composition described herein has a lymphocyte count of about $100/mm^3$, $200/mm^3$, $300/mm^3$, $400/mm^3$, $500/mm^3$, or $600/mm^3$ or about $100/mm^3$ to $400/mm^3$, $200/mm^3$ to $400/mm^3$, $300/mm^3$ to $500/mm^3$, $300/mm^3$ to $600/mm^3$, $400/mm^3$ to $500/mm^3$, or $400/mm^3$ to $600/mm^3$. In a specific embodiment, a subject to be administered a cancer vaccine or composition described herein has a lymphocyte count greater than or equal to $400/mm^3$.

In certain embodiments, a subject to be administered a cancer vaccine or composition described herein has a platelet count of about $25,000/mm^3$, $50,000/mm^3$, $75,000/mm^3$, $100,000/mm^3$, $200,000/mm^3$, or $300,000/mm^3$ or about $25,000/mm^3$ to $100,000/mm^3$, $50,000/mm^3$ to $100,000/mm^3$, $75,000/mm^3$ to $100,000/mm^3$, $100,000/mm^3$ to $200,000/mm^3$, $100,000/mm^3$ to $300,000/mm^3$, or $200,000/mm^3$ to $300,000/mm^3$. In a specific embodiment, a subject to be administered a cancer vaccine or composition described herein has a platelet count greater than or equal to $100,000/mm^3$.

In certain embodiments, a subject to be administered a cancer vaccine or composition described herein has a hemoglobin count of about 5 g/dL, 10 g/dL, 15 g/dL, or 20 g/dL, or about 5 to 10 g/dL, 5 to 15 g/dL, 10 to 15 g/dL, or 10 to 20 g/dL. In a specific embodiment, a subject to be administered a cancer vaccine or composition described herein has a hemoglobin count greater than or equal to 10 g/dL.

In certain embodiments, a subject to be administered a cancer vaccine or composition described herein has AST, ALT, GGT, LDH, and alkaline phosphatase levels within 1, 1.5, 2, 2.5, or 3 times the upper normal limit. In a specific embodiment, a subject to be administered a cancer vaccine or composition described herein has AST, ALT, GGT, LDH, and alkaline phosphatase levels within 2.5 times the upper normal limit.

In certain embodiments, a subject to be administered a cancer vaccine or composition described herein has a total bilirubin of about 1 mg/dL, 1.5 mg/dL, 2 mg/dL, 2.5 mg/dL, or 3 mg/dL, or about 1.5 to 2.5 mg/dL, 1.5 to 3 mg/dL, 2 to 2.5 mg/dL, or 2 to 3 mg/dL. In a specific embodiment, a subject to be administered a cancer vaccine or composition described herein has total bilirubin greater than or equal to 2 mg/dL.

In certain embodiments, a subject to be administered a cancer vaccine or composition described herein has serum creatinine levels within 0.5, 1, 1.5, 2, 2.5, or 3 times the upper normal limit. In a specific embodiment, a subject to be administered a cancer vaccine or composition described herein has serum creatinine levels within 1.5 times the upper normal limit.

In certain embodiments, a subject to be administered a cancer vaccine or composition described herein has coagulation tests PT and PTT that are within 0.5, 1, 1.5, 2, 2.5, or 3 times the normal limits. In certain embodiments, a subject to be administered a cancer vaccine or composition described herein has coagulation tests PT and PTT that are within normal limits.

6.6.4 Combination Therapies

In certain embodiments, the methods provided herein for preventing, treating, and/or managing brain cancer comprise administering to a patient (e.g., a human patient) in need thereof a prophylactically and/or a therapeutically effective regimen, the regimen comprising administering to the patient a cancer vaccine or composition described herein and one or more additional therapies, said additional therapy not being a cancer vaccine or composition described herein. The cancer vaccine or composition described herein and the additional therapy can be administered separately, concurrently, or sequentially. The combination therapies can act additively or synergistically.

The combination therapies can be administered to a subject in the same pharmaceutical composition. Alternatively, the combination therapies can be administered concurrently to a subject in separate pharmaceutical compositions. The combination therapies may be administered to a subject by the same or different routes of administration.

Any therapy (e.g., therapeutic or prophylactic agent) which is useful, has been used, or is currently being used for the prevention, treatment, and/or management of cancer (e.g., brain cancer) can be used in combination with a cancer vaccine or composition described herein in the methods described herein. Therapies include, but are not limited to, peptides, polypeptides, antibodies, conjugates, nucleic acid molecules, small molecules, mimetic agents, synthetic drugs, inorganic molecules, and organic molecules. Non-limiting examples of cancer therapies include chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy. In certain embodiments, a prophylactically and/or therapeutically effective regimen of the invention comprises the administration of a combination of therapies.

In one embodiment, the prior chemotherapy is temozolomide. In embodiment, the prior therapy is radiation therapy. In another embodiment, the prior therapy is a combination of temozolomide and radiation therapy. In a preferred embodiment, the combination of temozolomide and radiation are administered using the Stupp regimen. In another preferred embodiment, the combination of temozolomide, Avastin® (bevacizumab) and radiation are administered. In another embodiment, the prior therapy is surgery. In some embodiments, the patient undergoes surgery before the initiation of combination therapy. In some embodiments, the patient undergoes surgery before treatment with temozolomide. In some embodiments, the patient undergoes surgery before the initiation of radiation therapy. In each of these embodiments that describe the use of combination therapy, the cancer vaccine may be administered before, during, or after the treatment of the patient with the therapy that is being combined. In a preferred embodiment, the patient has failed Avastin® (bevacizumab) therapy prior to the administration of the cancer stem cell targeted vaccine. In another preferred embodiment, the patient has failed Avastin® (bevacizumab) therapy prior to the administration of the cancer stem cell targeted vaccine, and remains on Avastin® (bevacizumab) during treatment with the cancer stem cell targeted vaccine.

Examples of cancer therapies which can be used in combination with a cancer vaccine or composition described herein include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; histone deacetylase inhibitors (HDACs) gemcitabine hydrochloride; hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman;

piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies which can be used in combination with a cancer vaccine or composition described herein include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, MA; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™ (see U.S. Patent Pub. No. US 2002/0168360 A1, dated Nov. 14, 2002, entitled "Methods of Preventing or Treating Inflammatory or Autoimmune Disorders by Administering Integrin αvβ3 Antagonists in Combination With Other Prophylactic or Therapeutic Agents"); vorozole; zanoterone; zeniplatin; zilascorb; and zinostatin stimalamer.

In some embodiments, the therapy(ies) used in combination with a cancer vaccine or composition described herein is an immunomodulatory agent. "Immunomodulatory agents" can also be called "adjuvants", and the two terms are used interchangably herein. Non-limiting examples of immunomodulatory agents which can be used in combination with a cancer vaccine or composition described herein include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent. In a preferred embodiment, the immunomodulatory agent is GM-CSF. In another preferred embodiment, the immunomodulatory agent is imiquimod. In another preferred embodiment, both GM-CSF and imiquimod are used as immunomodulatory agents.

In some embodiments, the therapy(ies) used in combination with a cancer vaccine or composition described herein is an anti-angiogenic agent. Non-limiting examples of anti-angiogenic agents which can be used in combination with a cancer vaccine or composition described herein include proteins, polypeptides, peptides, conjugates, antibodies (e.g., human, humanized, chimeric, monoclonal, polyclonal, Fvs, ScFvs, Fab fragments, F(ab)2 fragments, and antigen-binding fragments thereof) such as antibodies that specifically bind to TNF-α, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In a preferred embodiment, the anti-angiogenic therapy is bevacizumab (Avastin®). In other embodiments, the therapy(ies) used in accordance with the invention is not an anti-angiogenic agent.

In some embodiments, the therapy(ies) used in combination with a cancer vaccine or composition described herein is an anti-inflammatory agent. Non-limiting examples of anti-inflammatory agents which can be used in combination with a cancer vaccine or composition described herein include any anti-inflammatory agent, including agents useful in therapies for inflammatory disorders, well-known to one of skill in the art. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), and methylxanthines (e.g., theophylline (UNIPHYL™, THEO-DUR™, SLO-BID™, AND TEHO-42™)). Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™) corticosteroids (e.g., methylprednisolone (MEDROL™)), cortisone, hydrocortisone, prednisone (PREDNISONE™ and DELTASONE™), prednisolone (PRELONE™ and PEDIA-PRED™), triamcinolone, azulfidine, and inhibitors of eicosanoids (e.g., prostaglandins, thromboxanes, and leukotrienes. Other examples of anti-inflammatory agents can be found, e.g., in U.S. Publication No. 005/0002934 A1 at paragraphs 290-294, which is incorporated by reference in its entirety. In other embodiments, the therapy(ies) used in accordance with the invention is not an anti-inflammatory agent.

In certain embodiments, the therapy(ies) used in combination with a cancer vaccine or composition described herein is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, cholormbucil, cyclophosphamide, ifosfamide, decarbazine, mechlorethamine, melphalan, and temozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine).

Currently available cancer therapies and their dosages, routes of administration and recommended usage are known in the art and have been described in such literature as the Physician's Desk Reference (60th ed., 2006). In accordance with the present invention, the dosages and frequency of administration of chemotherapeutic agents are described supra.

6.6.5 Biological Assays

The cancer vaccines and compositions described herein can be tested for their ability to treat, prevent, or manage brain cancer.

6.6.5.1 In Vivo Assays

The cancer vaccines and compositions described herein can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the vaccine components, whether such vaccine components are administered separately or as an admixture, and the frequency of administration of the vaccine components.

Animal models for cancer can be used to assess the efficacy of a cancer vaccine or composition described herein or a combination therapy described herein. Examples of animal models for brain cancer include, but are not limited to, xenograft studies using brain cancer cell lines that express IL-13Rα2, or primary human tumor cells that express IL-13Rα2. In these models, mice are immunized to induce an IL-13Rα2-specific T cell response, which is then evaluated for its ability to inhibit the growth of the tumor. In one embodiment, the tumor xenograft forms prior to the immunization to test the ability of the IL-13Rα2-specific T cell response to inhibit the growth of the preexisting tumor. In another embodiment, the IL-13Rα2-specific T cell response is induced prior to the injection of the tumor cells, to evaluate the ability of the immune response to prevent the formation of a tumor.

6.6.5.2 Cytotoxicity Assays

The toxicity and/or efficacy of the cancer vaccines and compositions described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic regimens that exhibit large therapeutic indices are preferred. While therapeutic regimens that exhibit toxic side effects may be used, care should be taken to design a delivery system that targets such agents to the site of affected tissue in order to minimize potential damage to uninfected cells and, thereby, reduce side effects.

6.7 Articles of Manufacture

Also encompassed herein is a finished packaged and labeled pharmaceutical product. This article of manufacture includes the appropriate unit dosage form in an appropriate vessel or container such as a glass vial or other container that is hermetically sealed. The pharmaceutical product may contain, for example, the components of a cancer vaccine described herein in a unit dosage form.

In a specific embodiment, the unit dosage form is suitable for parenteral, intravenous, intramuscular, intranasal, or subcutaneous delivery. Thus, encompassed herein are solutions, preferably sterile, suitable for each delivery route.

As with any pharmaceutical product, the packaging material and container are designed to protect the stability of the product during storage and shipment. Further, the products provided herein include instructions for use or other informational material that advise the physician, technician, or patient on how to appropriately prevent or treat brain cancer in question. In other words, the article of manufacture includes instruction means indicating or suggesting a dosing regimen including, but not limited to, actual doses, monitoring procedures, and other information.

Specifically, provided herein is an article of manufacture comprising packaging material, such as a box, bottle, tube, vial, container, sprayer, insufflator, intravenous (i.v.) bag, envelope and the like; and at least one unit dosage form of a vaccine or pharmaceutical composition described herein contained within said packaging material, wherein said vaccine or pharmaceutical composition described herein comprises a cancer vaccine described herein, and wherein said packaging material includes instruction means which indicate that said IL-13Rα2 peptide-based vaccine described herein can be used to prevent, manage, and/or treat brain cancer or one or more symptoms thereof by administering specific doses and using specific dosing regimens as described herein.

EXAMPLES

The following examples further illustrate the invention but, of course, should not be construed as in any way limiting its scope.

7.1 Example 1

This example demonstrates that EphA2 and IL-13Rα2 are cancer stem cell antigens.

7.1.1 Materials and Methods

Flow cytometry was performed on the brain cancer cell line A-172 to assess the expression of EphA2 and IL-13Rα2 on these cancer cells. The experimental protocol included the following steps.

A-172 cells were thawed and plated in 10 cm culture dishes under sterile conditions and using aseptic technique. The A-172 cells were grown in MEM containing 10% FBS. Both cell lines were grown at 37° C. with 5% $CO_2$ in humidified air. The A-172 cells were passaged 1:5 every 3 days.

On the day of the experiments, the cells were washed once with 1x PBS and incubated for 3 minutes with 2 ml 0.25% trypsin-EDTA at 37° C. The cells were then detached from the tissue culture plates with gentle agitation and diluted with 10 ml of DMEM. The cells then were placed in a 50 ml conical tube and centrifuged at 350×g for 5 minutes. The supernatant was aspirated and the cells were resuspended in 10 ml DMEM. Fifty μl of the cells were mixed with an equal volume of trypan blue and the mixture was carefully placed on a hemacytometer for counting. The cell volumes were then adjusted with DMEM to a concentration of $5\times10^6$/ml.

Twenty flow cytometry tubes Fisher Scientific) were prepared and 100 μl of the cells were added to each tube ($5\times10^5$ cells/tube) (10 tubes with A-172 cells).

Twenty μl of Fc blocking reagent was added to each tube and the tubes were incubated at room temperature for 10 minutes.

Ten μl of each antibody, as provided in Table 1, below, was diluted to the described working concentration provided in Table 2, below, and was added to each appropriate tube. The tubes were incubated for 30 minutes at 4° C. with gentle agitation.

TABLE 1

| | | | | A-172 CELLS | | | | | |
|---|---|---|---|---|---|---|---|---|---|
| Tube | #1 | #2-3 | #4-5 | #6 | #7 | #8 | #9 | #10 |
| Primary Antibody | Unstained | Isotype control | Secondary Antibodies Alone | α-CD133 | α-IL13Rα2 | α-EphA2 | α-CD133 + α-IL13Rα2 | α-CD133 + α-EphA2 |
| Secondary Antibody | | Anti-mouse OR Anti-goat | Anti-mouse OR Anti-goat | Anti-mouse | Anti-goat | Anti-goat | Anti-mouse + Anti-goat | Anti-mouse + Anti-goat |

TABLE 2

| Antibody | Working Concentration |
|---|---|
| CD133 | 16.5 μg/ml |
| IL13Rα2 | 10 μg/ml |
| EphA2 | 50 μg/ml |
| Anti-mouse-APC | 1:200 |
| Anti-goat-FITC | 1:200 |

After the incubation, the cells were centrifuged at 300×g for 1 minute in a tabletop, refrigerated microcentrifuge. The supernatant was removed and the cells were washed with ice cold FACS buffer 3 times. The cells were then resuspended in 100 μl of FACS buffer and 10 μl of the secondary antibodies was added to the appropriate tubes. The tubes were incubated for 30 minutes at 4° C. with gentle agitation in the dark.

After the incubation, the cells were centrifuged at 300×g for 1 minute in a tabletop, refrigerated microcentrifuge. The supernatant was removed and the cells were washed with ice cold FACS buffer 3 times. The cells were then resuspended in 200 μl of FACS buffer and analyzed on a FACSCalibur (BD Biosciences) flow cytometer.

7.1.2 Results

In brain cancer, the brain cancer stem cells can be identified using the marker CD133, i.e., brain cancer stem cells are known to express the CD133 antigen (see, e.g., Singh et al., 2004, Nature 432:396-401, the disclosure of which is hereby incorporated by reference in its entirety). The cancer stem cells of the brain cancer cell line A-172 express CD133 (see, e.g., Qiang et al., 2009, Cancer Letters 271:13-21, the disclosures of which is hereby incorporated by reference in its entirety).

Figure 1B:
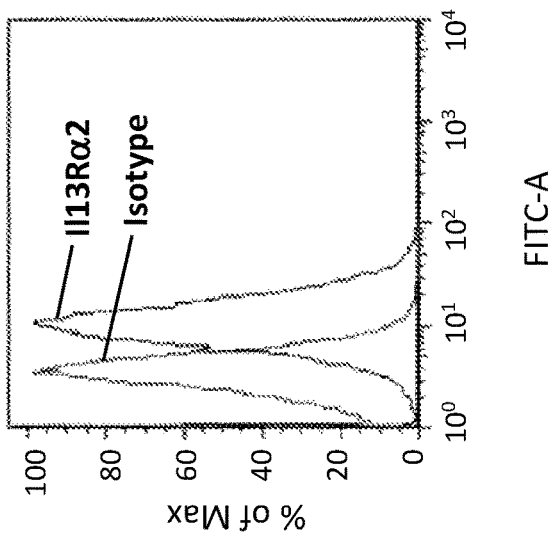
Figure 1A:
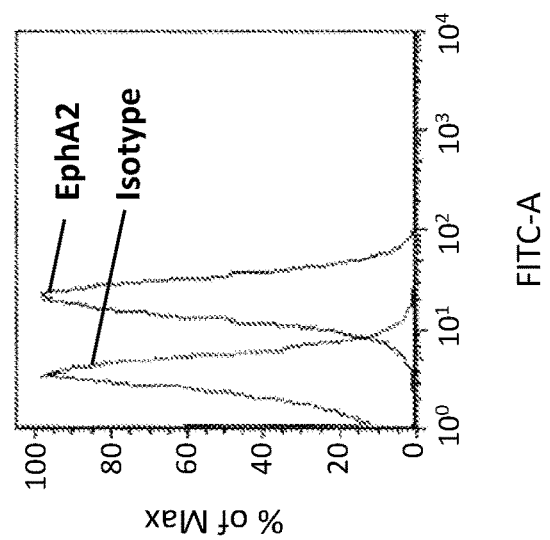
Figure 2B:
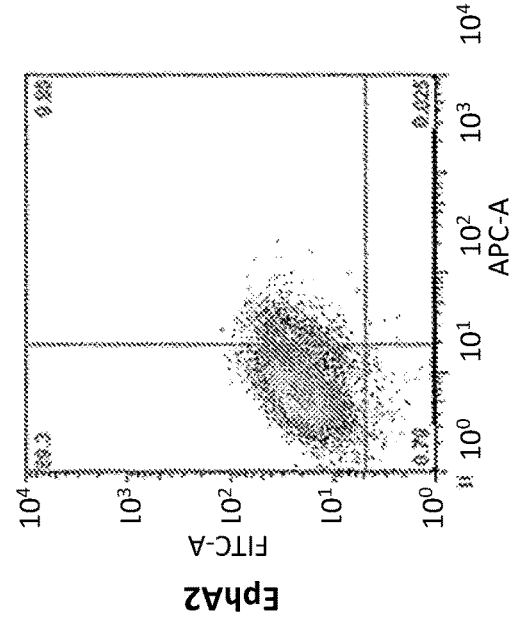
FIGS. 2A-2D depict joint staining of CD133 and EphA2 cells of the A-172 cancer cell line (FIGS. 2A and 2C), and demonstrates that CD133+ cells of the cell line also express EphA2 (FIGS. 2B and 2D).
Figure 2A:
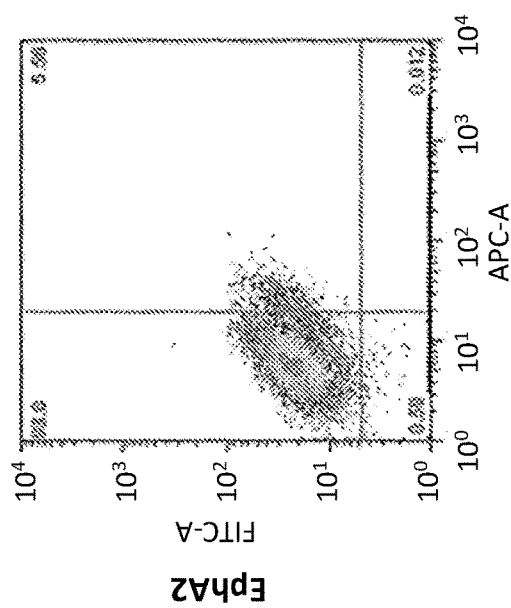
Figure 2D:
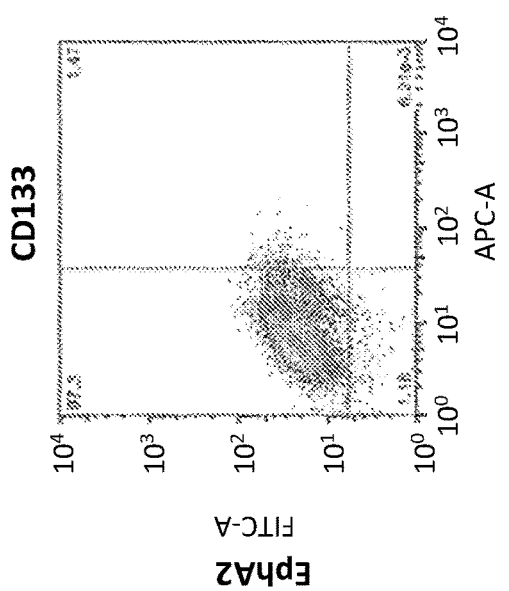
Figure 2C:
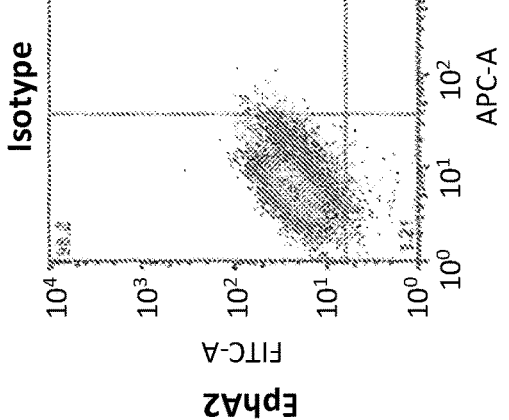

As demonstrated in FIGS. 1A-1C, all cells of the A-172 line were positive for EphA2 (FIG. 1A) and IL-13Rα2 (FIG. 1B), whereas a small population of such cells also were positive for CD133 (FIG. 1C). This CD133+ cell subpopulation thus represents the cancer stem cell subpopulation of the A-172 cell line, and the same expression pattern of CD133 on A-172 cells was observed in a subsequent duplicate experiment (see FIGS. 6A-6C and 7A-7D).

As demonstrated in FIGS. 2A-2D, the CD133+ population also was positive for expression of EphA2, thus demonstrating that EphA2 is present on the cancer stem cell population obtained from the A-172 cell line, and thus that EphA2 is a cancer stem cell antigen.

Figure 4:
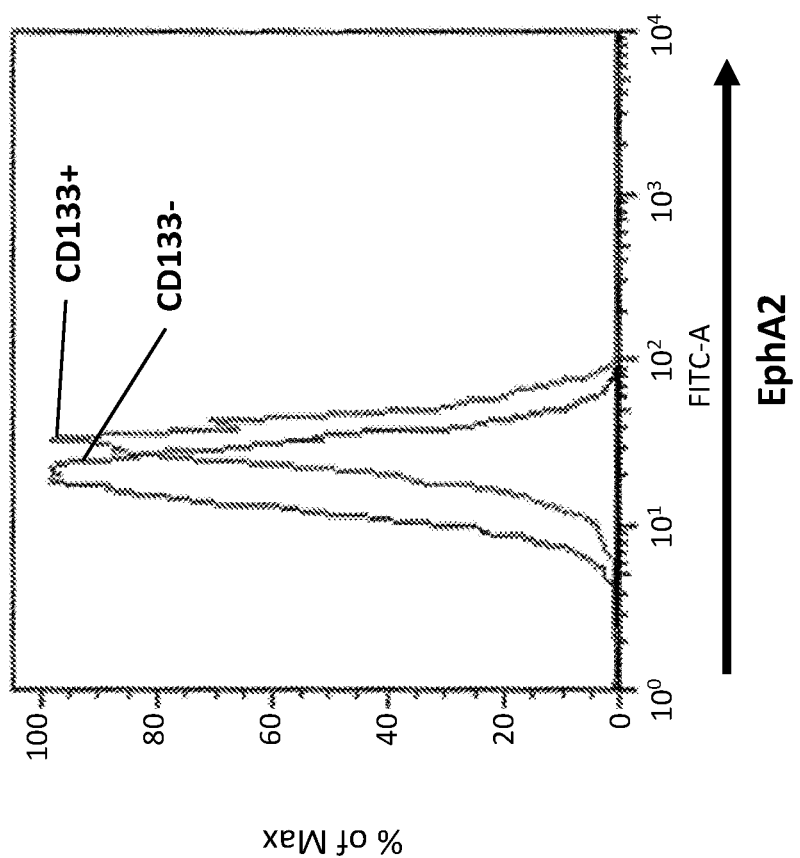
FIG. 4 shows that CD133+ cells of the A-172 cancer cell line also express EphA2.
Figure 5:
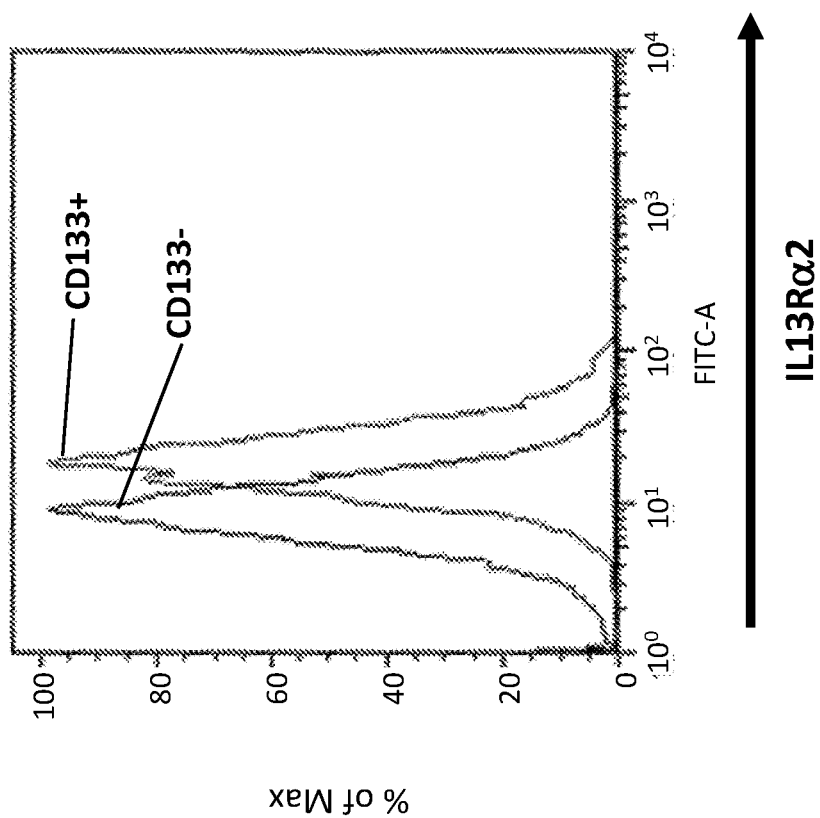
FIG. 5 shows that CD133+ cells of the A-172 cancer cell line also express IL-13Rα2.
Figure 8A:
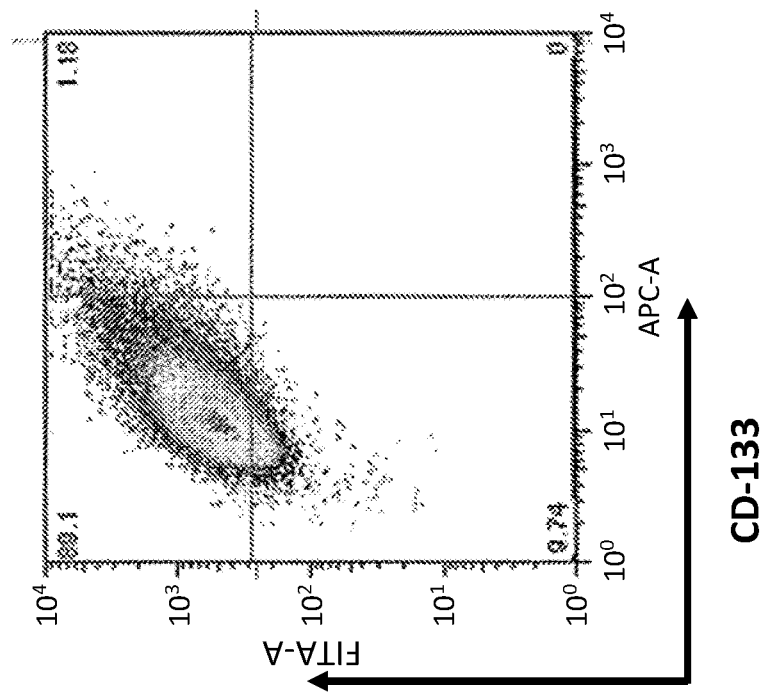
FIGS. 8A-8B demonstrate that CD133+ cells of the A-172 cancer cell line also express EphA2 (FIG. 8A) and IL-13Rα2 (FIG. 8B).
Figure 8B:
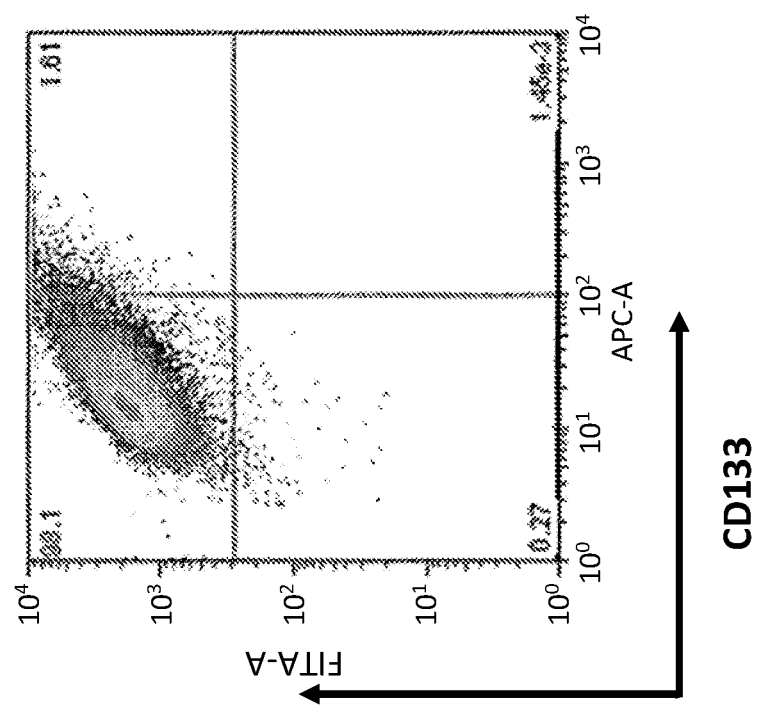

This fact was verified in a subsequent duplicate experiment (see FIG. 8A). Moreover, as shown in FIG. 4, EphA2 was expressed to higher levels on CD133+ Cells as compared to CD133− cells Similarly, as demonstrated by FIGS. 3A-3D, the CD133+ population of A-172 cell line also was positive for expression of IL-13Rα2, thus demonstrating that IL-13Rα2 is present on the cancer stem cell population obtained from the A-172 cell line, and thus that IL-13Rα2 is a cancer stem cell antigen. This fact was verified in a subsequent duplicate experiment (see FIG. 8B). Moreover, as shown in FIG. 5, IL-13Rα2 is was expressed to higher levels on CD133+ cells as compared to CD133− cells.

7.1.3 Conclusion

These data demonstrate that EphA2 is a cancer stem antigen, and thus can be used in methods for the treatment of cancer, such as brain cancer.

TABLE OF SEQUENCES

| SEQUENCE NO. | SEQUENCE | DESCRIPTION |
|---|---|---|
| 1 | Trp Leu Pro Phe Gly Phe Ile Leu Ile | Amino acid residues 345-353 of Interleukin-13 Receptor alpha |
| 2 | Trp Leu Pro Phe Gly Phe Ile Leu Val | Amino acid residues 345-353 of Interleukin-13 Receptor alpha with mutation of I to V at position 345 |
| 3 | Ala Leu Pro Phe Gly Phe Ile Leu Val | Amino acid residues 345-353 of Interleukin-13 Receptor alpha with mutation of W to A at position 345 and I to V at position 353 |
| 4 | Glu Leu Pro Phe Gly Phe Ile Leu Val | Amino acid residues 345-353 of Interleukin-13 Receptor alpha with mutation of W to E at position 345 and I to V at position 353 |

TABLE OF SEQUENCES-continued

| SEQUENCE NO. | SEQUENCE | DESCRIPTION |
| --- | --- | --- |
| 5 | Thr Leu Ala Asp Phe Asp Pro Arg Val | Amino acid residues 883-891 of EphA2 |
| 6 | Leu Thr Leu Gly Glu Phe Leu Lys Leu | Amino acid residues 96-104 of Survivin |
| 7 | Leu Met Leu Gly Glu Phe Leu Lys Leu | Amino acid residues 96-104 of Survivin with a Methionine substitution at position 2 |
| 8 | Glu Leu Thr Leu Gly Glu Phe Leu Lys Leu | Amino acid residues 95-104 of Survivin |
| 9 | Glu Leu Met Leu Gly Glu Phe Leu Lys Leu | Amino acid residues 95-104 of Survivin with a methionine substitution at position 3 |
| 10 | Ala Gln Tyr Ile Lys Ala Asn Ser Lys Phe Ile Gly Ile Thr Glu Leu | Tetanus Toxoid peptide |

EQUIVALENTS

The present invention is not to be limited in scope by the specific embodiments described herein. Indeed, various modifications of the invention in addition to those described will become apparent to those skilled in the art from the foregoing description. Such modifications are intended to fall within the scope of the appended claims.

Various publications, patents and patent applications are cited herein, the disclosures of which are incorporated by reference in their entireties.

We claim:

1. A method for treating brain cancer in a subject in need thereof comprising administering to said subject:

(i) a pharmaceutical composition comprising an IL-13Ra2 peptide having an amino acid sequence chosen from SEQ ID NOs: 1-4, an EphA2 peptide having the amino acid sequence set forth in SEQ ID NO:5, a survivin peptide having the amino acid sequence set forth in SEQ ID NO: 9, and a Tetanus toxoid peptide having the amino acid sequence set forth in SEQ ID NO:10, wherein said composition is formulated as an emulsion; and (ii) one or more T cell receptor modulators selected from anti-CD4 antibodies, anti-CD3 antibodies, anti-CD5 antibodies, anti-CD7 antibodies, anti-CD8 antibodies, anti-CD40 ligand monoclonal antibodies, anti-CD52 antibodies, anti-CD2 antibodies, anti-CD11a antibodies, anti-B7 antibodies, CTLA4-immunoglobulin, lymphocyte function-associated antigen-3 T cell inhibitor protein (LFA-3TIP), and combinations thereof;

wherein the method does not comprise administering a peptide consisting of SEQ ID NO: 7; and wherein the pharmaceutical composition is co-administered with bevacizumab.

2. The method of claim 1, wherein said composition is emulsified by Montanide ISA-51.

3. The method of claim 1, wherein said pharmaceutical composition is administered subcutaneously, and said one or more T cell receptor modulators are administered intravenously, subcutaneously, or intramuscularly.

4. The method of claim 1, wherein said subject is in remission, has undergone a relapse, and/or has received at least one prior treatment that failed.

5. The method of claim 1, wherein said method comprises the administration of at least one additional cancer therapy.

6. The method of claim 5, wherein said at least one additional cancer therapy is radiation, chemotherapy, or surgery.

7. The method of claim 1, wherein the IL-13Rα2 peptide comprises SEQ ID NO:3.

8. The method of claim 1, wherein the method further comprises the administration of one or more additional immunomodulatory agents.

9. The method of claim 8, wherein the one or more additional immunomodulatory agents are selected from nucleic acid molecules, toll-like receptor (TLR) agonists, and/or immune response modifiers that polarize the immune response of a subject toward a Th1 or Th2 response.

10. The method of claim 9, wherein the TLR agonist is a TLR3 agonist.

11. The method of claim 1, wherein the brain cancer is glioma, astrocytoma, glioblastoma, oligodendroglioma, brain stem glioma, ependymoma, or a mixed tumor comprising more than one glial cell types.

12. The method of claim 1, wherein said brain cancer is acoustic schwannoma, cranial pharyngioma, meningioma, or medulloblastoma.

13. The method of claim 8, wherein the one or more immunomodulatory agents is granulocyte-macrophage colony-stimulating factor (GM-CSF).

14. The method of claim 9, wherein the one or more TLR agonists is imiquimod.

\* \* \* \* \*

UNITED STATES PATENT AND TRADEMARK OFFICE
CERTIFICATE OF CORRECTION

| | | |
|---|---|---|
| PATENT NO. | : 12,357,678 B2 | Page 1 of 1 |
| APPLICATION NO. | : 18/308774 | |
| DATED | : July 15, 2025 | |
| INVENTOR(S) | : Ivan Bergstein, Christopher Brooks and Thomas P. Cirrito | |

It is certified that error appears in the above-identified patent and that said Letters Patent is hereby corrected as shown below:

In the Claims

In Claim 1, Column 45, Line 60, please change "IL-13Ra2" to -- IL-13Rα2 --.

Signed and Sealed this
Twenty-sixth Day of August, 2025

Coke Morgan Stewart
*Acting Director of the United States Patent and Trademark Office*

SEQUENCE LISTING

```
Sequence total quantity: 10
SEQ ID NO: 1            moltype = AA  length = 9
FEATURE                 Location/Qualifiers
REGION                  1..9
                        note = Amino acid residues 345-353 of IL-13 Receptor alpha
source                  1..9
                        mol_type = protein
                        organism = Homo sapiens
SEQUENCE: 1
WLPFGFILI                                                                 9

SEQ ID NO: 2            moltype = AA  length = 9
FEATURE                 Location/Qualifiers
REGION                  1..9
                        note = Amino acid residues 345-353 of IL-13 Receptor alpha
                          with mutation of I to V at position 345
source                  1..9
                        mol_type = protein
                        organism = synthetic construct
SEQUENCE: 2
WLPFGFILV                                                                 9

SEQ ID NO: 3            moltype = AA  length = 9
FEATURE                 Location/Qualifiers
REGION                  1..9
                        note = Amino acid residues 345-353 of IL-13 Receptor alpha
                          mutation of W to A at position 345 and I to V at position
                          353
source                  1..9
                        mol_type = protein
                        organism = synthetic construct
SEQUENCE: 3
ALPFGFILV                                                                 9

SEQ ID NO: 4            moltype = AA  length = 9
FEATURE                 Location/Qualifiers
REGION                  1..9
                        note = Amino acid residues 345-353 of IL-13 Receptor alpha
                          mutation W to E at position 345 and I to V at position 353
source                  1..9
                        mol_type = protein
                        organism = synthetic construct
```

```
SEQUENCE: 4
ELPFGFILV                                                                         9

SEQ ID NO: 5           moltype = AA  length = 9
FEATURE                Location/Qualifiers
REGION                 1..9
                       note = Amino acid residues 883-891 of EphA2
source                 1..9
                       mol_type = protein
                       organism = Homo sapiens
SEQUENCE: 5
TLADFDPRV                                                                         9

SEQ ID NO: 6           moltype = AA  length = 9
FEATURE                Location/Qualifiers
REGION                 1..9
                       note = Amino acid residues 96-104 of Survivin
source                 1..9
                       mol_type = protein
                       organism = Homo sapiens
SEQUENCE: 6
LTLGEFLKL                                                                         9

SEQ ID NO: 7           moltype = AA  length = 9
FEATURE                Location/Qualifiers
REGION                 1..9
                       note = Amino acid residues 96-104 of Survivin with a
                        Methionine substitution at position 2
source                 1..9
                       mol_type = protein
                       organism = synthetic construct
SEQUENCE: 7
LMLGEFLKL                                                                         9

SEQ ID NO: 8           moltype = AA  length = 10
FEATURE                Location/Qualifiers
REGION                 1..10
                       note = Amino acid residues 95-104 of Survivin
source                 1..10
                       mol_type = protein
                       organism = Homo sapiens
SEQUENCE: 8
ELTLGEFLKL                                                                        10

SEQ ID NO: 9           moltype = AA  length = 10
FEATURE                Location/Qualifiers
REGION                 1..10
                       note = Amino acid residues 95-104 of Survivin with a
                        methionine substitution at position 3
source                 1..10
                       mol_type = protein
                       organism = synthetic construct
SEQUENCE: 9
ELMLGEFLKL                                                                        10

SEQ ID NO: 10          moltype = AA  length = 16
FEATURE                Location/Qualifiers
REGION                 1..16
                       note = Tetanus Toxoid peptide
source                 1..16
                       mol_type = protein
                       organism = synthetic construct
SEQUENCE: 10
AQYIKANSKF IGITEL                                                                 16
```